(12) United States Patent
Donolato et al.

(10) Patent No.: US 9,784,735 B2
(45) Date of Patent: Oct. 10, 2017

(54) BIOSENSOR BASED ON THE MEASUREMENTS OF CLUSTERING DYNAMICS OF MAGNETIC PARTICLES USING A DOUBLE PASS SETUP

(71) Applicant: Danmarks Tekniske Universitet, Kgs. Lyngby (DK)

(72) Inventors: Marco Donolato, København K (DK); Filippo Bosco, København Ø (DK); Mikkel Fougt Hansen, Værløse (DK); Anja Boisen, Birkerød (DK); En-Te Hwu, Nankang Taipei (TW)

(73) Assignee: Danmarks Tekniske Universitet, Kgs. Lyngby (DK)

(*) Notice: Subject to any disclaimer, the term of this patent is extended or adjusted under 35 U.S.C. 154(b) by 127 days.

(21) Appl. No.: 14/900,339

(22) PCT Filed: Mar. 24, 2014

(86) PCT No.: PCT/EP2014/055882
§ 371 (c)(1),
(2) Date: Dec. 21, 2015

(87) PCT Pub. No.: WO2014/206583
PCT Pub. Date: Dec. 31, 2014

(65) Prior Publication Data
US 2016/0146798 A1    May 26, 2016

(30) Foreign Application Priority Data
Jun. 28, 2013 (EP) .................................... 13174311

(51) Int. Cl.
*G01N 33/543* (2006.01)
*G01N 21/17* (2006.01)
*G01N 33/50* (2006.01)

(52) U.S. Cl.
CPC ... *G01N 33/54333* (2013.01); *G01N 21/1717* (2013.01); *G01N 33/50* (2013.01);
(Continued)

(58) Field of Classification Search
CPC ....... G01N 33/54333; G01N 33/54373; G01N 33/50; G01N 2021/1727; G01N 21/1717
See application file for complete search history.

(56) References Cited

U.S. PATENT DOCUMENTS

| | | |
|---|---|---|
| 4,725,140 A | 2/1988 | Musha et al. |
| 7,639,359 B2 | 12/2009 | Chung et al. |

(Continued)

FOREIGN PATENT DOCUMENTS

| | | |
|---|---|---|
| DE | 43 12 320 A1 | 10/1994 |
| EP | 2 492 665 A1 | 8/2012 |

OTHER PUBLICATIONS

International Search Report for PCT/EP2014/055882 dated Jun. 16, 2014.

*Primary Examiner* — Shogo Sasaki
(74) *Attorney, Agent, or Firm* — Knobbe Martens Olson & Bear LLP

(57) ABSTRACT

Disclosed herein is a biosensor for optical detection of Brownian relaxation dynamics of magnetic particles measured by light transmission. The magnetic particles can be functionalized with biological ligands for the detection of target analytes in a sample. The setup may be implemented in a disc and optical pick-up head configuration.

10 Claims, 11 Drawing Sheets

(52) U.S. Cl.
CPC ............. *G01N 33/54373* (2013.01); *G01N 2021/1727* (2013.01)

(56) References Cited

U.S. PATENT DOCUMENTS

| | | | |
|---|---|---|---|
| 2003/0003464 A1 | 1/2003 | Phan et al. | |
| 2003/0219713 A1* | 11/2003 | Valencia | G01N 15/1475 435/4 |
| 2005/0185569 A1* | 8/2005 | Coombs | B01L 3/5027 369/275.4 |
| 2009/0033935 A1* | 2/2009 | Chung | B82Y 15/00 356/338 |
| 2012/0014836 A1* | 1/2012 | Dittmer | G01N 33/54326 422/69 |

\* cited by examiner

BIOSENSOR BASED ON THE MEASUREMENTS OF CLUSTERING DYNAMICS OF MAGNETIC PARTICLES USING A DOUBLE PASS SETUP

CROSS-REFERENCE TO RELATED APPLICATIONS

This application is a U.S. National Phase Application of PCT International Application Number PCT/EP2014/055882, filed on Mar. 24, 2014, designating the United States of America and published in the English language, which is an International Application of and claims the benefit of priority to European Patent Application No. 13174311.4, filed on Jun. 28, 2013. The disclosures of the above-reference applications are hereby expressly incorporated by reference in their entireties.

The invention relates to a novel two-pass biosensor adapted for rapid and sensitive detection of target analytes utilizing magnetic nanoparticles.

BACKGROUND

Magnetic nanoparticles and magnetic nanobeads (MNBs), i.e., superparamagnetic nanoparticles embedded in a polymeric matrix, represent a widely spread tool in modern biomedical technologies. In particular their utilization in different biosensing schemes has been explored in the last few years. The long-range interaction between magnetic nanoparticles and an external magnetic field enables easy manipulation and sensitive detection. The main advantages offered by biosensing approaches utilizing magnetic fields and magnetic carriers are that biological media have an intrinsic low magnetic susceptibility and the magnetic interactions are generally not affected by surface charges, pH values, ionic concentrations or temperature. In addition, the realization of a microfluidic device based on magnetic carriers to capture, sort and detect target analytes in biological media is particularly appealing, due to the potential low-cost, simplicity of the device and high sensitivity achievable.

U.S. Pat. No. 7,639,359 discloses a method for detection of analytes by measuring single particle dynamics of bio-functionalized magnetic nanoparticles. The method in U.S. Pat. No. 7,639,359 comprises applying linearly polarized light to a suspension of bio-functionalized nanoparticles subjected to an oscillating uniaxial magnetic field and subsequently measure how the polarization of the light rotates when passing through the magnetic nanoparticles suspension. In this case the signal monitored is in the first harmonic with respect to the magnetic field excitation.

One disadvantage with the method disclosed in U.S. Pat. No. 7,639,359 is that it is complex, it relies on a very small signal due to light polarization rotation and consequently the setup is costly in that it requires optical elements such as aligned polarizers in order to ensure that the rotation of the light polarization is correctly measured. Another disadvantage with the method disclosed in U.S. Pat. No. 7,639,359 is that it requires single domain magnetic nanoparticles in order to work that these are generally not efficient light scatters.

US20120003750 discloses a method for detection of an analyte by measuring the dynamics of analyte-driven cluster formation of bio-functionalized superparamagnetic particles. The method in US20120003750 comprises allowing the superparamagnetic particles in a suspension to form analyte-driven clusters in the presence of a rotating magnetic field and thereafter measure the intensity and amplitude of the scattered light at higher harmonics of the driving frequency.

One disadvantage of the method disclosed in US20120003750 is the requirement of electromagnets creating a rotating in-plane magnetic field. Having electromagnets generating a rotating field will take up more space thus limiting practical implications such down-sizing of the biosensing setup or integration of the setup into other systems. In addition the signal due to scattered light from magnetic beads at a large angle from the incident light is extremely low, especially for particles of few hundreds nm of diameter, and a large area and very sensitive photodetector or photomultiplier is needed.

DESCRIPTION OF THE INVENTION

Disclosed herein is a biosensor comprising at least one optical reservoir containing a suspension of magnetic particles. The biosensor further comprises a light source emitting light at a wavelength $\lambda$, with an intensity I, the light source being directed at the optical reservoir and being adapted for interacting with the suspension of magnetic particles, wherein the light source is an optical pickup head and wherein the light entering the optical reservoir has an intensity $I_{in}$, and light transmitted through the optical reservoir has an intensity $I_{trans}$.

The biosensor further also comprises a magnetic field generation unit generating an oscillating uniaxial magnetic field, the oscillating uniaxial magnetic field oscillating at a frequency $f_x$ being variable between a start frequency $f_{x, start}$ and an end frequency $f_{x, end}$, the oscillating uniaxial magnetic field being applied to the optical reservoir containing the suspension of magnetic particles whereby the suspension of magnetic particles is modulated such that the intensity $I_{trans}$ of light transmitted through the suspension of magnetic particles is modulated compared to the intensity $I_{in}$ of the light entering the optical reservoir, wherein light from the light source and the oscillating uniaxial magnetic field is propagating substantially parallel along an incoming direction.

The biosensor also comprises a reflecting object positioned such that the modulation of the intensity $I_{trans}$ of the light transmitted through the suspension of magnetic particles in the optical reservoir, and/or light transmitted through the optical reservoir without being modulated by the suspension of magnetic particles, is reflected back through the optical reservoir by the reflecting object along a direction of propagation being substantially parallel with the incoming direction.

The biosensor also comprises a detection unit measuring the intensity $I_{trans}$ of the light transmitted through the suspension of magnetic particles in the optical reservoir after the light has passed through the optical reservoir at least two times.

By using the at least two time passing of the light in the optical reservoir, a very compact biosensor is obtainable. The biosensor is further simple, flexible and inexpensive, since only few elements are required. There is further a variety of options for exchanging individual parts in the setup. Importantly, any kind of light source can be introduced into the system that does not require linearly polarized light, laser light sources or polarizers that per definition will increase both complexity and cost of the biosensor.

The oscillating uniaxial magnetic field used in the biosensor is beneficial in that it lowers the overall space requirements making the biosensor suitable for implementation into a variety of devices. By measuring the intensity of the modulated transmitted light, and not the polarization change of the light, it is possible to record measurements even after the light has been transmitted through the sample multiple times further increasing the flexibility of the biosensor.

In one or more embodiments the magnetic particles are functionalized with a bioactive ligand, such as e.g. antibodies, DNA, RNA, peptides, proteins, or protein complexes. The bioactive ligand is able to bind to/capture target/analyte molecules in a sample to be analysed, whereby the existence of this target/analyte is easily detectable. The term target/analyte molecules also include cells or bacteria.

In one or more embodiments the magnetic particles have a non-zero remnant magnetic moment.

In one or more embodiments the magnetic particles are present in the suspension with a concentration in the range of 0.1 µg/mL to 2000 µg/mL. Alternatively, the suspension concentration can be in the range of 0.1 µg/mL to 1000 µg/mL, or in the range of 0.1 µg/mL to 500 µg/mL, or in the range of 1 µg/mL to 50 µg/mL.

In one or more embodiments the magnetic particles are magnetic beads, such as e.g. magnetic polymeric beads.

In one or more embodiments the magnetic particles are substantially spherical. By substantially spherical is meant that the individual particles have negligible optical anisotropy in the oscillating uniaxial magnetic field. Alternatively, the magnetic particles can have an irregular potato-type shape, but still with a negligible optical anisotropy of an ensemble of individual particles in the oscillating uniaxial magnetic field.

In one or more embodiments the substantially spherical magnetic particles have a diameter between 10 and 3000 nm. The particles may also be between 20 and 1000 nm or between 50 and 250 nm.

In one or more embodiments the biosensor further comprises a microfluidic system comprising at least one optical reservoir and at least one sample injection system for e.g. injection, dilution and mixing of the suspension of magnetic particles and the sample to be analyzed. This allows for on-site and in-device preparation and measurements of a sample, which reduces the complexity and makes the biosensor very easy to use.

In one or more embodiments the sample injection system comprises at least one microcapillary valve and at least one microneedle for injection, dilution and mixing of the suspension of magnetic particles and the sample to be analyzed in the at least one microcapillary valve.

In one or more embodiments the biosensor comprises a plurality of optical reservoirs and/or microfluidic systems implemented on a disc, or a similar device. The plurality of optical reservoirs may contain functionalized magnetic particles, wherein the functionalized magnetic particles in each of the plurality of optical reservoirs can be different from the functionalized magnetic particles in the other optical reservoirs or be similar. Thereby simultaneous analysis of multiple target molecules and/or multiple samples is possible.

In one or more embodiments one or more types of particles are mixed together. The different types of particles can have different sizes, different properties such as being either magnetic or non-magnetic, or in case of magnetic particles they can have different magnetic susceptibilities.

In one or more embodiments the magnetic particles can be functionalized with or can incorporate a fluorescent dye.

In one or more embodiments the biosensor further comprises a motor adapted for rotating the plurality of optical reservoirs such that simultaneous analysis of the functionalized magnetic particles in each of the plurality of optical reservoirs each positioned at different coordinates on the disc surface is possible, and a digital track area positioned on the disc surface, each of the digital track area storing information about the position of each of the plurality of optical reservoirs on the disc surface and/or the type of functionalized magnetic particles contained in each of the optical reservoirs. In that way it is possible to always keep track of which optical reservoir that the measurements are performed on at a given time.

In one or more embodiments the magnetic field generation unit is an electromagnet generating an AC magnetic field having a magnetic field intensity.

In one or more embodiments the magnetic field generation unit is an electromagnet generating a time varying magnetic field between $f_{x,\,start}$=0.1 Hz and $f_{x,\,end}$=10 kHz, the magnetic field having a magnetic field intensity between 0.1 mT and 5 mT.

In one or more embodiments the light source is a laser.

In one or more embodiments the detection unit is a photo-detector.

In one or more embodiments the light source and the detection unit is integrated into the optical pickup head, e.g. from/in a device such as a CD player/recorder, a DVD player/recorder or a Blu-ray player/recorder.

In one or more embodiments DVD laser light and Blu-ray laser light from the compact disc reader device is alternated thereby allowing for simultaneous measurement of light transmitted from the optical reservoirs and tracking of the position of the optical reservoir on the disc surface.

In one or more embodiments the biosensor is used for diagnostic purposes. These uses may e.g. by for analyzing blood, salvia, urine, water, plasma, or serum.

The biosensor is primarily for measuring dynamic behaviours of magnetic particles driven by the oscillating uniaxial magnetic field. Alternatively, the biosensor can also be used for time-resolved measurements of the relaxation of the particles after the application of an external magnetic field.

The detection scheme used in the measurements using the biosensor described above may include a modulation/variation of the intensity of the light from the light source and/or a modulation of the magnetic field at, where the signal, which is detected, is at an integer combination of the frequency of the light intensity modulation from the light source and the frequency of the magnetic field.

Detection of the target molecule/cell/bacteria can be achieved by measuring the increase of the hydrodynamic diameter of the particles when the target molecule binds on the specifically functionalized particle surface.

Detection of the target molecule/cell/bacteria can also be achieved by target molecule induced aggregates formation of specifically functionalized magnetic particles of the same type (i.e. agglutination assay).

Further, detection of the target molecule/cell/bacteria may be achieved by target molecule induced aggregate formation of specifically functionalized particles of different types such as magnetic/nonmagnetic, particles of different sizes or by having fluorescent dyes on the surface.

These are three of the most general way one can use this system as a biosensor.

BRIEF DESCRIPTION OF THE DRAWINGS

FIG. 3a show the temporal variation of the transmitted light in the measurement configuration of FIG. 2a and FIG. 3b shows the Fast Fourier Transform (FFT) of the photodetector signal using the setup of FIG. 2a.

FIG. 4 illustrates a frequency sweep measured in the measurement configuration of FIG. 2a.

FIGS. 10a-b show a modified version of the biosensor with FIG. 10b being a close-up of the optical reservoir in shown in FIG. 10a.

DESCRIPTION OF PREFERRED EMBODIMENTS

Figure 1:
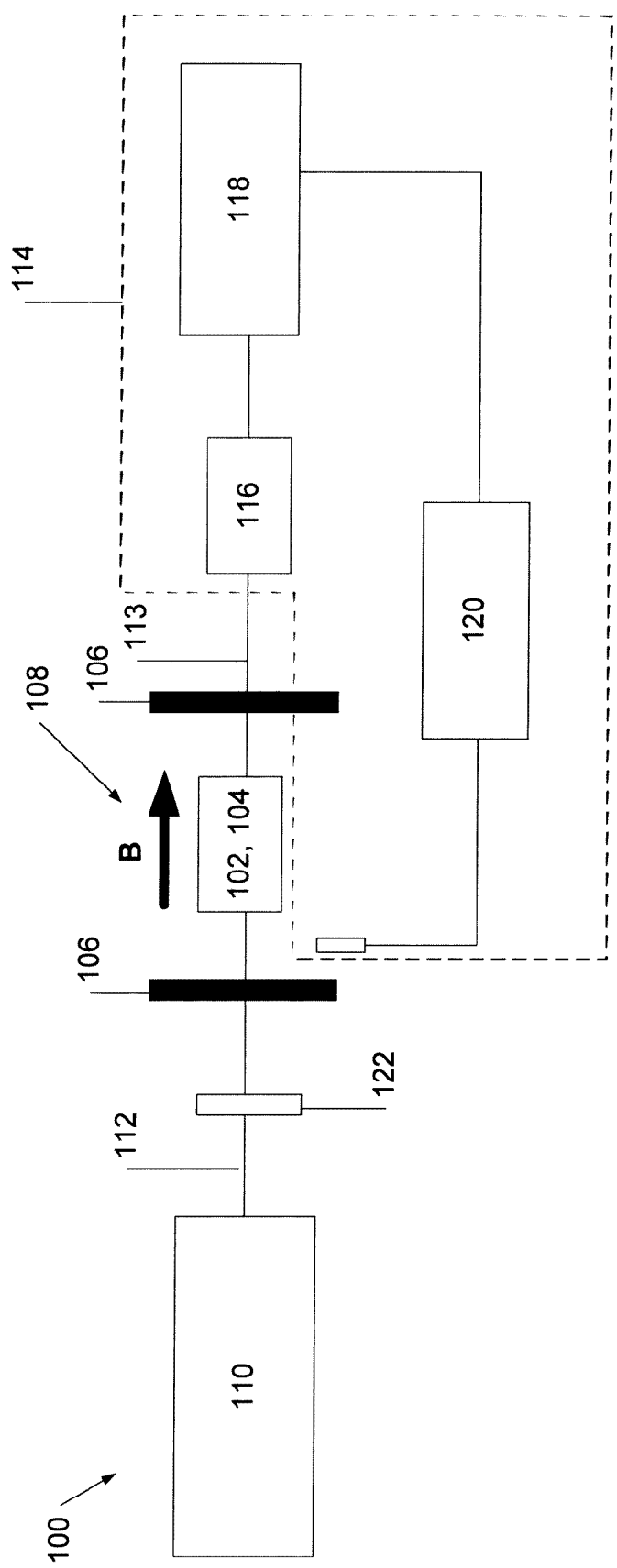
FIG. 1 illustrates a biosensor setup.

FIG. 1 shows an embodiment of the biosensor 100 for detection of analytes. The detection principle is based on measurements of the dynamic behaviour of magnetic nanoparticles driven by an oscillating uniaxial magnetic field by measuring the intensity $I_{trans}$ of the light transmitted through the suspension of nanoparticles. Alternatively, the biosensor can also be used for time-resolved measurements of the relaxation of the particles after the application of the magnetic field.

Detection of the target molecule/cell/bacteria can be achieved by measuring the increase of the hydrodynamic diameter of the particles when the target molecule binds on the specifically functionalized particle surface.

Detection of the target molecule/cell/bacteria can also be achieved by target molecule induced aggregates formation of specifically functionalized magnetic particles of the same type (i.e. agglutination assay).

Further, detection of the target molecule/cell/bacteria may be achieved by target molecule induced aggregate formation of specifically functionalized particles of different types such as magnetic/nonmagnetic, particles of different sizes or by having fluorescent dyes on the surface.

These are three of the most general way one can use this system as a biosensor

The biosensor 100 comprises a suspension of magnetic particles 102 in an optical reservoir 104. The magnetic particles suspended in the solution 102 may be substantially spherical particles, in the sense that individual particles have negligible optical anisotropy. Alternative shapes such as e.g. ellipsoidal or ovoid-shaped particles (irregular-shaped) can also be used. The magnetic particles may also be magnetic beads such as magnetic polymeric beads.

The suspension of magnetic particles may include more than one type of particles mixed together. The different types of particles can have different sizes, or different properties such as being either magnetic or non-magnetic (as long as one of the particles types is magnetic). In case the particles are all magnetic particles they can have different magnetic susceptibilities. The sizes of the individual particles types may vary from being nano-sized particles to being micron-sized particles. The use of bigger particles can block the rotation of smaller particles if a target molecule is present.

The magnetic particles may be functionalized with a bioactive ligand, such as e.g. antibodies, DNA, RNA, peptides, proteins, or protein complexes. The magnetic particles may also be functionalized with a fluorescent dye.

The magnetic particles will normally have a non-zero remnant magnetic moment.

The optical reservoir 104 is illustrated as a cuvette in FIG. 1 but alternatives such as different forms of microfluidic devices could also be imagined. A microfluidic system comprising microcapillary valves, microneedle for injection, dilution and mixing of the sample to be analyzed and similar could also be used in combination with the optical reservoirs.

The biosensor 100 comprises a magnetic field generation unit 106 generating a oscillating uniaxial magnetic field 108. The oscillating uniaxial magnetic field 108 is applied to the optical reservoir 104 containing the suspension of magnetic particles 102 as illustrated in FIG. 1. The magnetic field generation unit can e.g. be an electromagnet generating an AC magnetic field having a magnetic field intensity. The frequency of the AC magnetic field will normally be between 0.1 Hz and 10 kHz. The magnetic field intensity will normally be between 0.1 mT and 5 mT.

The biosensor also comprises a light source 110 directed at the optical reservoir 104. The light 112 from the light source 110 is adapted for interacting with the suspension of magnetic particles 102. The light source could be a laser emitting light in e.g. the ultra violet (UV), visible or infrared (IR) spectral range, a UV lamp, a light emitting diode (LED) or similar. The emitted light will normally be linearly polarized when exiting the light source.

Normally, a light source 110 will emit light at a wavelength $\lambda$ with an intensity I. The light entering the optical reservoir 104 will have an intensity $I_{in}$ and light transmitted through the optical reservoir will have an intensity $I_{trans}$. The magnetic field generation unit 106 will normally generate an oscillating uniaxial magnetic field oscillating at a frequency $f_x$ being variable between a start frequency $f_{x,\,start}$ and an end frequency $f_{x,\,end}$.

Figure 2B:
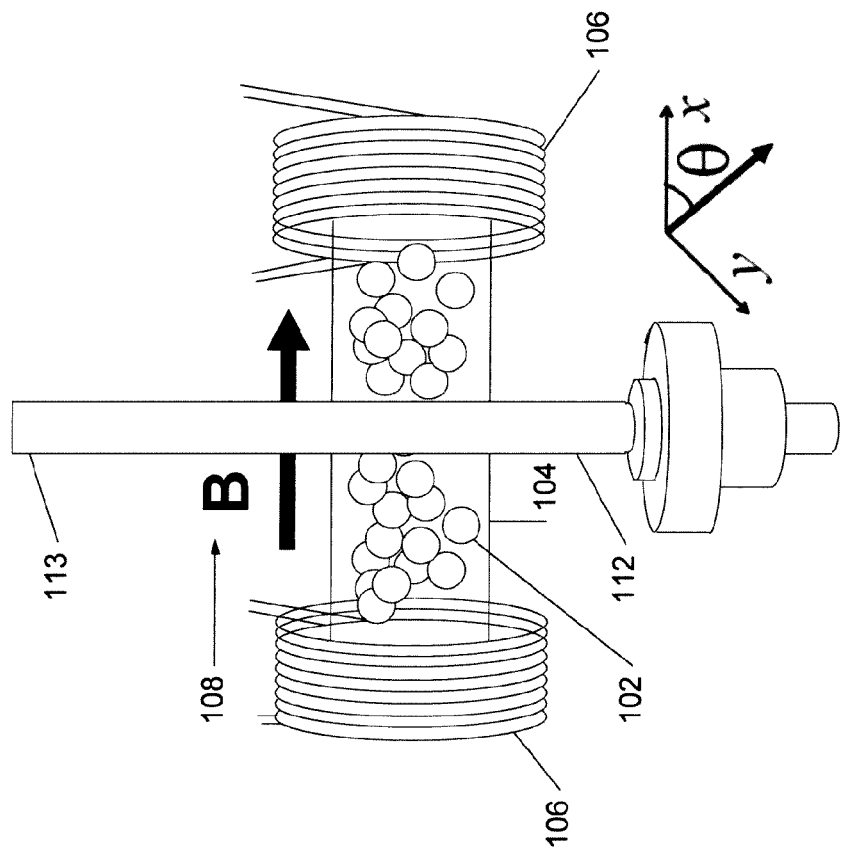
FIGS. 2a-b show two different measurement configurations.
Figure 2A:
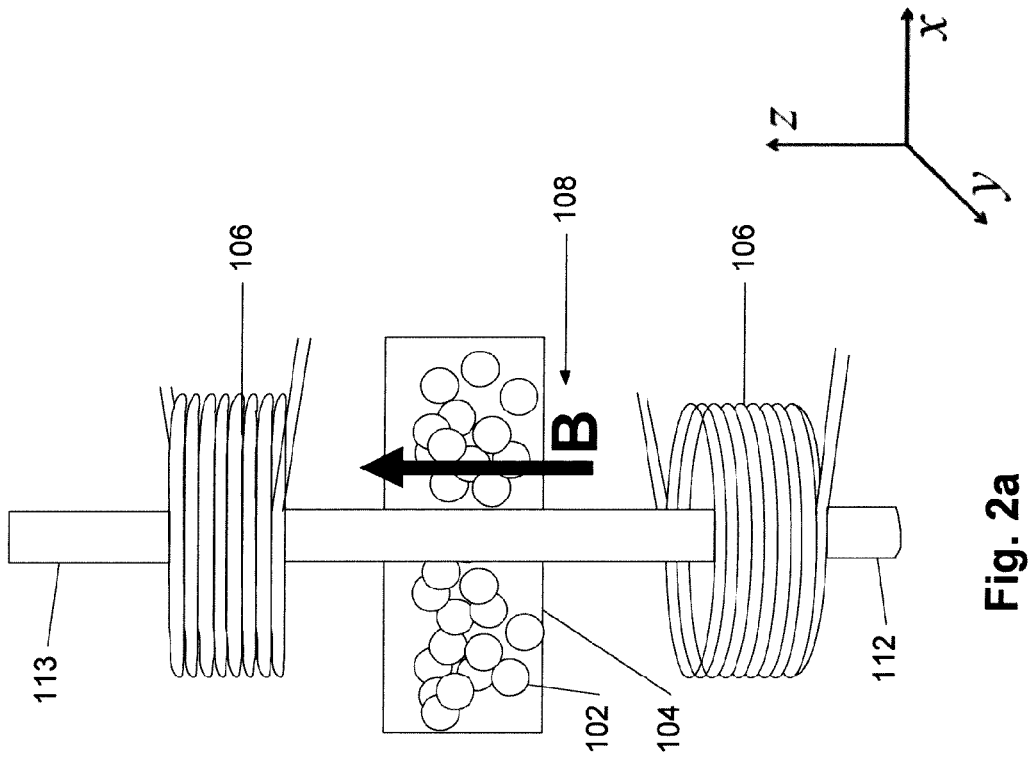

In FIG. 1, the light 112 from the light source 110 and the oscillating uniaxial magnetic field 108 from the magnetic field generation unit 106 propagate parallel with each other towards the optical reservoir 104. FIG. 2a shows this measurement setup in a close-up view. Alternatively, a perpendicular measurement configuration could also be imaging as shown in FIG. 2b.

The biosensor 100 in FIG. 1 further comprises a detection unit 114 measuring components of the frequency $f_y$ of the transmitted light being different from the first harmonic component $f_x$. These frequencies could be the $2^{nd}$ or higher harmonic components of light 113 transmitted from the suspension of magnetic particles 102 in the optical reservoir 104. Normally, the frequency $f_y$ varying between a start frequency $f_{y,\,start}$ and an end frequency $f_{y,\,end}$ as the oscillating uniaxial magnetic field is swept from the start frequency $f_{x,\,start}$ to the end frequency $f_{x,\,end}$ will be detected.

In FIG. 1, the detection unit 114 comprises a photodiode 116, a lock-in amplifier 118, and a gauss meter 120. Different detection units could also be used without changing the scope of this invention. A polarizer may also be positioned between the light source and the optical reservoir.

The light source 110 used for producing the experimental data described and shown in the subsequent figures are obtained using a COHERENT laser emitting light with a wavelength of λ=633 nm. The signals are likewise collected by a ThorLabs PDA36A photodetector while the beam is expanded to a final diameter of 5 mm with an adjustable LINOS beam expander (not shown in the figure). The magnetic field is measured real time with a Hall-probe (not shown in the drawing).

The self-inductance of the magnetic coils used was corrected for to maintain a constant field amplitude vs frequency. The signal was filtered using a signal recovery 7225 computer controlled lock-in amplifier. The dynamic light scattering measurements were performed with a Malvern Zetasizer Nano device.

When a magnetic field is applied to a suspension of magnetic particles, an optical anisotropy is induced in the medium due to the formation of linear chains of particles aligned with the field. This anisotropy leads to the phenomena of linear dichroism, i.e., different attenuation of the transmitted light for different polarization components of the light due to different adsorption and/or scattering. The formation dynamics of linear chains is dominated by the Brownian rotation of the particles and this can be sensed by light transmission/scattering.

The present method relies on the dynamic breaking and reforming of particle clusters and the formation of permanent clusters in the presence of biomolecular recognition. This approach is fundamentally different from the rotation dynamics of the clusters presented in US20120003750. There, the equilibrium cluster size (which is constant over a field cycle) in a rotating magnetic field gives a modulation of the scattered light. Typically, magnetic beads with a non-zero remnant moment is used for these measurements. In the approach, disclosed in this application, clusters are dynamically disrupted and reformed during a cycle of the axially varying magnetic field resulting in a modulation of the transmitted optical signal. Thus, the signal in the present approach is given by the ability of the individual particles to align with the axial magnetic field and reform magnetic chains and this is typically done with particles with a remnant magnetic moment. The dynamics of these magnetic nanoparticles is governed by their ability to align their remnant magnetic moment by a physical rotation of the individual particles (Brownian rotation) and to reform the particle clusters. The Brownian relaxation frequency is characterized by:

$$f_B = \frac{k_B T}{6\pi \eta V_h} \quad \text{Eq. 1}$$

where $k_B$ is the Boltzmann's constant, T is the absolute temperature, $V_h$ is the hydrodynamic particle volume and $\eta$ is the dynamical viscosity of the fluid.

Upon excitation by a weak alternating magnetic field (with $H_{AC}(t)=H_0 \sin(2\pi f t)$), the magnetization m(t) of e.g. magnetic nanoparticles change due to their physical rotation. In the time domain, the magnetization can be written as $$m(t)=m_{AC} \sin(\omega t-\phi) \quad \text{Eq. 2}$$

where φ is the phase lag between the magnetization response and the excitation and $m_{AC}$ is the frequency dependent amplitude of the magnetization.

In the frequency domain, the magnetic nanoparticle response is characterized by the complex magnetic susceptibility:

$$\chi=\chi'-i\chi''=|\chi|(\cos \phi - i \sin \phi) \quad \text{Eq. 3}$$

with in-phase component χ' and out-of-phase component χ". At low frequencies, the magnetization of the magnetic nanoparticles responds in-phase with the applied magnetic field (φ=0). Upon increasing the frequency, the magnetic nanoparticles magnetization will lag behind the applied field and χ' will decrease monotonically. Correspondingly, χ" first increases to assume its maximum value when f=$f_B$ and decreases above $f_B$.

The magnetic susceptibility of a bead ensemble is well described by $$\chi = \chi' - i\chi'' = \frac{\chi_0 - \chi_\infty}{1+(if/f_B)^{1-\alpha}} + \chi_\infty \quad \text{Eq. 4}$$

where $\chi_0$ and $\chi_\infty$ are the magnetic susceptibilities for f=0 and f=∞, respectively, and α is a parameter accounting for polydispersity (α=0 for a monodisperse ensemble of magnetic nanoparticles).

The normalized magnetic susceptibility is defined by $$\tilde{\chi}=\chi/\chi_0=\tilde{\chi}'-i\tilde{\chi}''=|\tilde{\chi}|(\cos \phi - i \sin \phi) \quad \text{Eq. 5}$$

which fulfills that $\tilde{\chi}(0)=1$ and $\tilde{\chi}(\infty)=\chi_\infty/\chi_0$.

Sufficiently small or weakly magnetic interacting magnetic nanoparticles with negligible optical anisotropy of the individual particles show no significant agglomeration in zero applied magnetic field indicating that the thermal energy is larger than the magnetic interaction energy due to the remnant moment.

Consequently, the light transmitted by the solution of nanoparticles will show negligible optical anisotropy when no magnetic field and/or analyte is present. Magnetic nano-beads are examples of magnetic nanoparticles showing negligible optical anisotropy when they are not clustered.

In the measurement configuration shown in FIG. 2a, the oscillating uniaxial magnetic field 108 is applied parallel to light 112 from the light source 110—in this figure being a laser beam—propagation direction. This configuration will be denoted B∥k in the following.

For the majority of particle sizes, the transmitted signal for the B∥k configuration is maximal when the field is large, which is consistent with the fact that chains are formed along the light path that decrease the geometrical cross-section of the suspension. When the magnetic field approaches zero after positive saturation, the chains break up or become loosely bound due to thermal agitation.

When the field changes sign, the particles have to rotate physically to align their remnant magnetic moments with the field. When the Zeeman energy of a single magnetic nanoparticle is larger than the interaction energy with its neighbors, this will result in a rotation of the individual particles rather than a rotation of chains of particles. In this case, the observed dynamics therefore consists of (1) disruption of magnetic nanoparticle chains due to thermal agitation and/or the sign change of the magnetic field, (2) rotation of the individual magnetic nanoparticles trying to align with the magnetic field, and (3) reformation of magnetic nanoparticle chains. Hence, the time scale for the diffusion and rotation of the individual magnetic nanoparticles sets the time scale for the reforming of magnetic nanoparticle chains that give rise to the modulation of the optical signal.

In another measurement configuration as shown in FIG. 2b, the uniaxial magnetic field 108 is applied perpendicular to light 112 from the light source 110—in this figure being a laser beam—propagation direction. This configuration will be denoted (B⊥k) in the following.

When the oscillating uniaxial magnetic field is applied perpendicular to the laser beam direction (B⊥k) a polarizer 122 is introduced in the optical beam between the laser and the optical reservoir containing the particles to define a linear polarization at an angle θ to the magnetic field direction, where the angle θ with the x-axis is as sketched in the lower right part of FIG. 2b.

The optical signal that is symmetric with respect to the magnetization orientation of a chain may in a simple manner be explained by:

$$V(t) = V_{offset} + V_{AC} \sin^2(\omega t - \phi) \quad \text{Eq. 6}$$

where $V_{AC}$ is the frequency-dependent amplitude of the signal modulation, $V_{offset}$ is the signal offset and where we have neglected possible higher order terms of even powers of $\sin(\omega t - \phi)$. $V_{AC}$ has the same frequency dependence as the magnetic susceptibility, such that $$V_{AC} = V_0 |\tilde{\chi}| \quad \text{Eq. 7}$$

where $V_0$ is the amplitude for $f \to 0$. By recording the $2^{nd}$ harmonic component of the signal by the light transmitted in the magnetic nanobeads suspension, it is possible to precisely record and distinguish the frequency response of magnetic nanobeads having diameters of 50 nm, 130 nm and 250 nm. This is showed and discussed further in FIG. 8.

The $2^{nd}$ harmonic signal $$V_2 = V_2' + iV_2'' \quad \text{Eq. 8}$$

is measured by lock-in technique to be $$V_2' = -\frac{1}{2\sqrt{2}}(V_0|\tilde{\chi}|)^2 \sin(2\phi) = -\frac{1}{\sqrt{2}} V_0^2 (\tilde{\chi}')(\tilde{\chi}'') \quad \text{Eq. 9}$$

$$V_2'' = -\frac{1}{2\sqrt{2}}(V_0|\tilde{\chi}|)^2 \cos(2\phi) = -\frac{1}{2\sqrt{2}} V_0^2 [(\tilde{\chi}')^2 - (\tilde{\chi}'')^2]$$

Figure 3A:
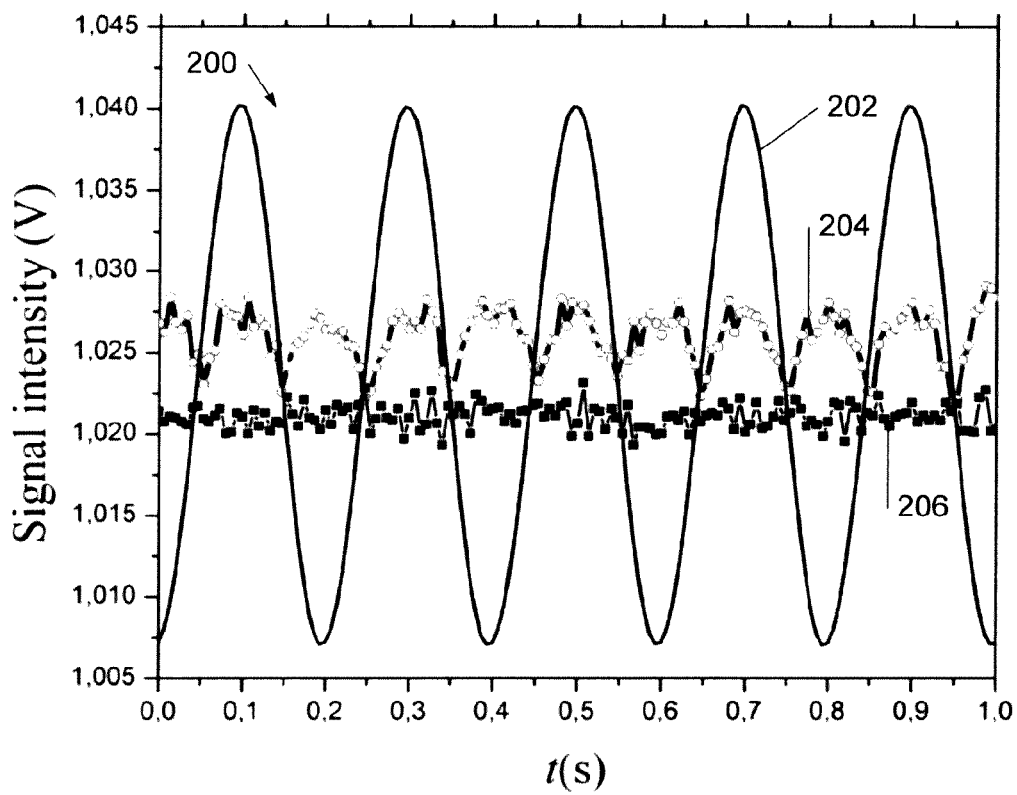

FIG. 3a shows the temporal variation 200 of the transmitted light in configuration B∥k for a suspension of magnetic nanobeads with a size of 50 nm in diameter and a concentration of 10 μg MNB/mL suspension. Line 202 indicates the oscillating external magnetic field waveform, while line 204 and line 206 represent the measured AC component of the photodetector signal under or in absence of the oscillating uniaxial magnetic field.

The applied field has an amplitude of 1 mT and f=5 Hz. In the figure is sketched the position of the magnetic bead clusters along the z-direction in the field maxima region.

In FIG. 3a the measurement configuration comprises a laser source (λ=633 nm), a transparent circular fluidic cell having diameter 5 mm and height, corresponding to the optical path in the liquid, of 1 mm. The cell, which has a volume of roughly 20 μL, is surrounded by two miniaturized electromagnets for generating the AC magnetic field and a photo detector. The optical cell may also be a cuvette or a microfluidic device.

The laser spot size can be expanded up to ~5 mm diameter by means of an adjustable beam expander in order to interact with the largest possible number of particles. In both cases, the amplitude of the applied magnetic field ranges between 1 and 3 mT. The AC magnetic field is measured in real time using a high-speed Hall probe that also provides the reference for a lock-in amplifier used to filter and detect the $2^{nd}$ harmonic voltage output from the photo detector in-phase and out-of-phase with the AC driving field. In an embodiment the frequency of the AC field is between 0.1 Hz and 10 kHz and the magnetic field has an intensity between 0.1 mT and 5 mT.

In the measurements described in the following, the optical effect which is measured due to the formation of magnetic particle chains in suspension can have a different sign. This depends on whether more or less light is transmitted when the field is maximum with respect to when it is zero again depending on the bead size, bead clustering state and/or the wavelength of the light used. This is discussed further in FIG. 9b.

In FIG. 3a, the signal level for the measurements obtained with no magnetic field excitation, line 206, is the same before and after an experiment. The signal with the field excitation, line 204, is dominated by a component at 2f, and shows sharp minima when the applied field intensity is close to zero and maxima when the field is numerically large. The signal level of the minima is close to that obtained when no magnetic field excitation is applied.

Figure 3B:
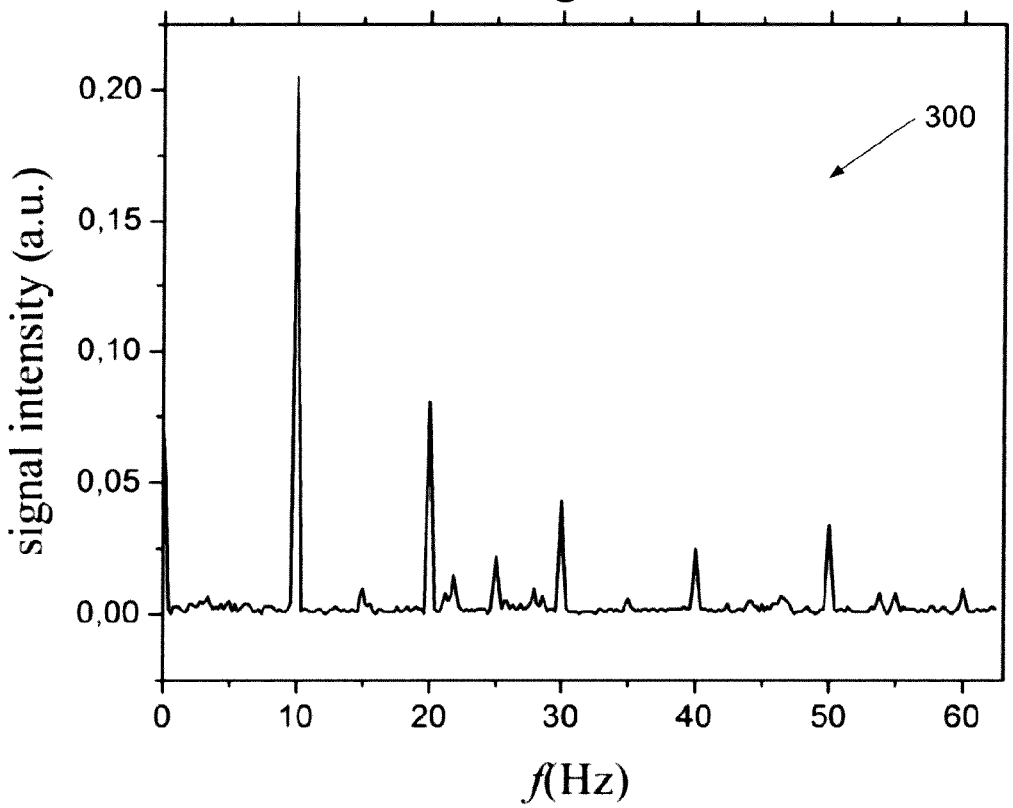

FIG. 3b shows the Fast Fourier Transform (FFT) 300 of the same photodetector signal as in FIG. 3a. FIG. 3b confirms the results form FIG. 3 in that the signal is dominated by a 2f component at 10.1 Hz, although weaker higher order even harmonics are also present.

Figure 4:
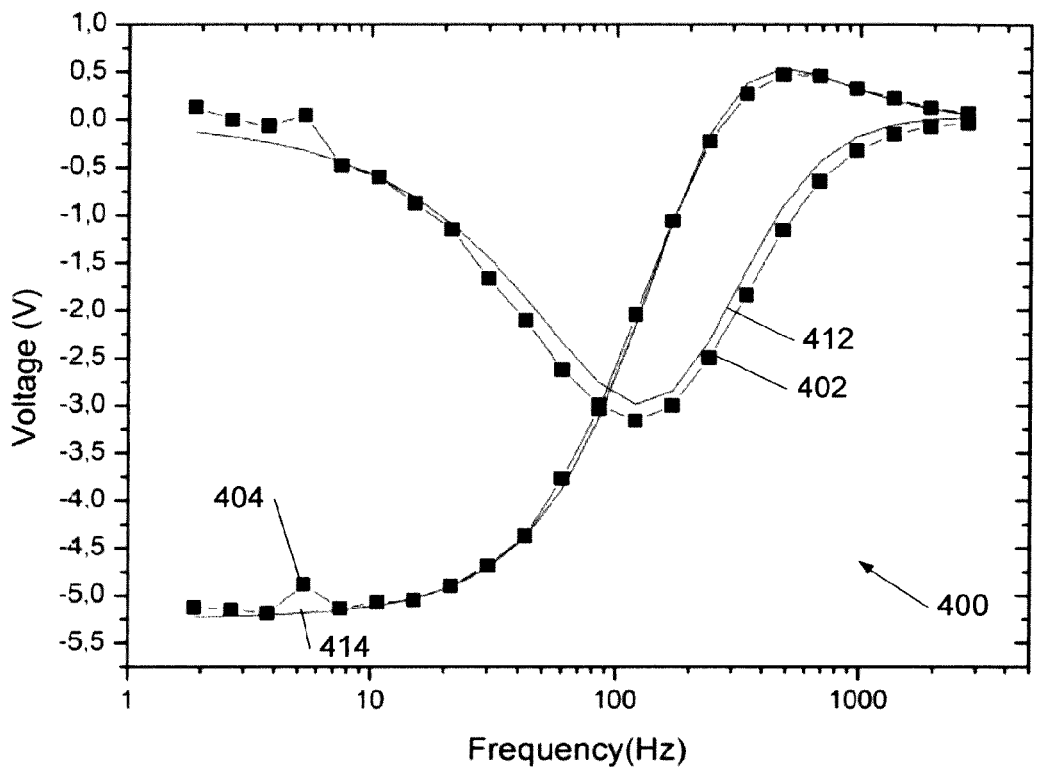

FIG. 4 shows the frequency sweep 400 measured in the configuration B∥k for the suspension of MNBs of 50 nm diameter and concentration 50 μg/mL. FIG. 4 illustrates the complex $2^{nd}$ harmonic signal 400 measured by lock-in technique vs. frequency of the applied magnetic field. The measured in-phase signal ($V_2'$) 402 has a clear peak near about 100.1 Hz whereas the out-of-phase signal ($V_2''$) 404 shows a step-like transition with saturation at low frequencies and a value close to zero at high frequencies. The solid lines 412, 414 indicates the fits of the curve for the in-phase signal ($V_2'$ signal) 402 and the out-of phase signal ($V_2''$ signal) 404 using the Eq.(9).

Figure 5A:
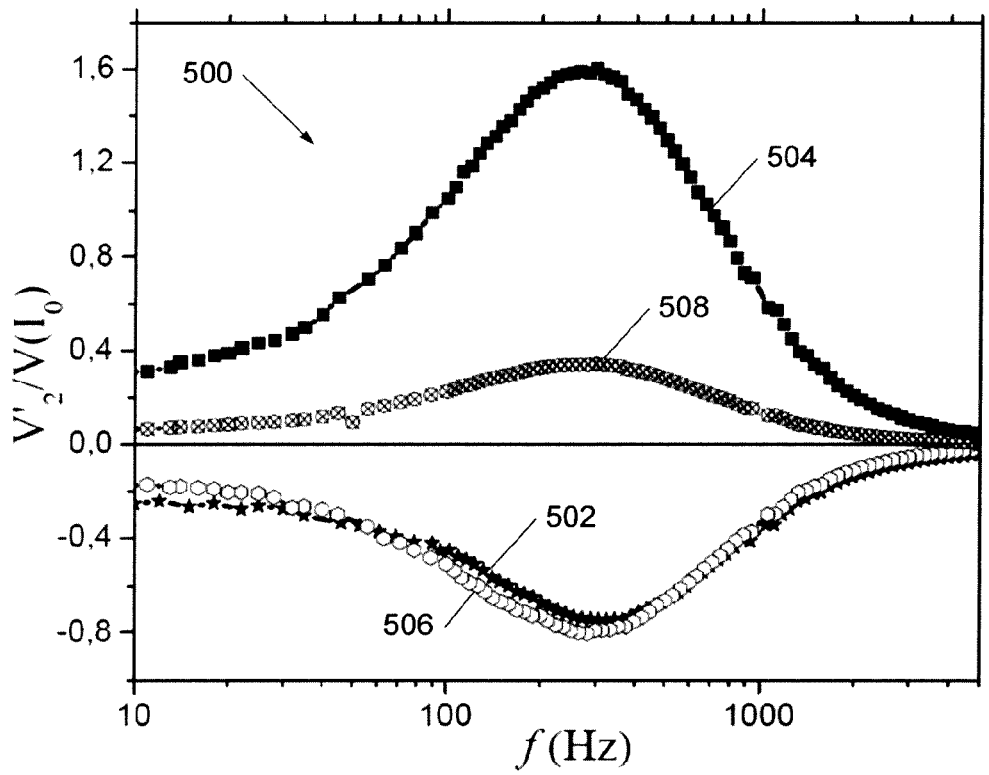
FIGS. 5a-c show in-phase and out-of phase $2^{nd}$ harmonic signals recorded for a suspension of magnetic beads at different measurement configurations.
Figure 5B:
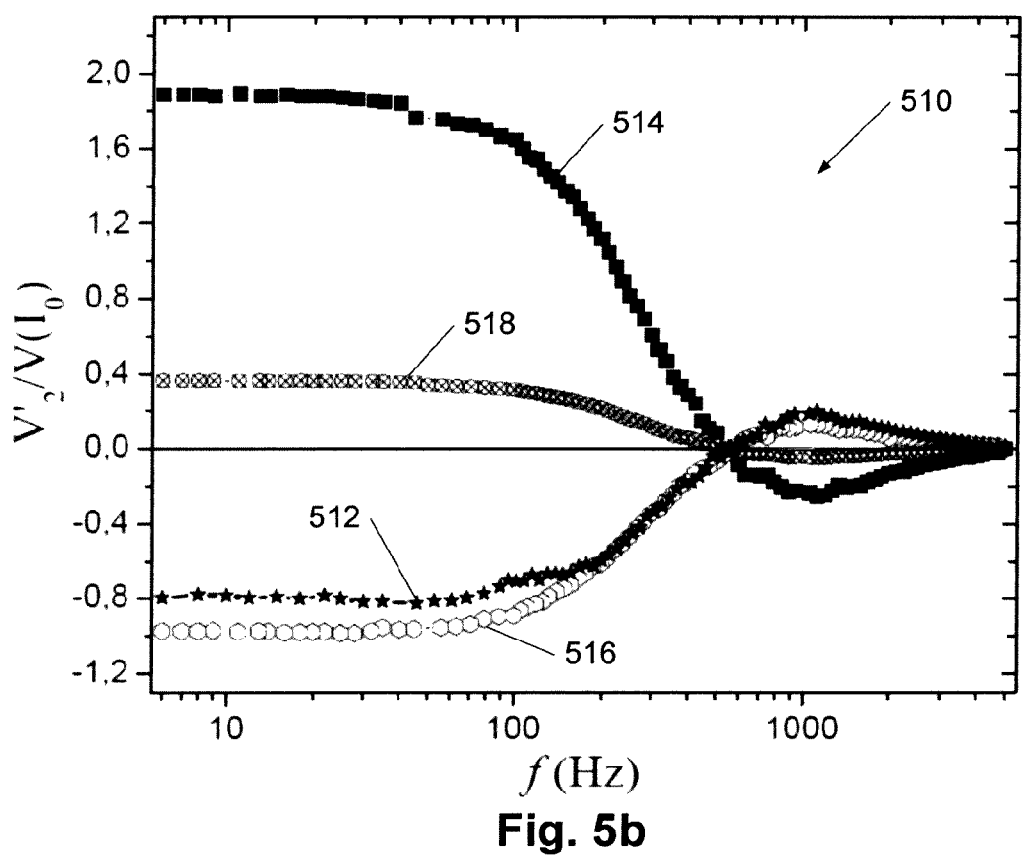

FIGS. 5a and 5b show a comparison of the data collected on the same MNBs suspension using different experimental configurations with the $V_2'$ signal 500 and the $V_2''$ signal 510 displayed in FIGS. 5a and 5b, respectively. The data are recorded for a suspension of 50 nm magnetic beads at a concentration 10 μg/mL.

The signals are measured at four different measurement configurations; lines 502 and 512 are measured with the configuration B∥k, lines 504 and 514 with the configuration B⊥k and θ=0°, lines 506 and 516 with the configuration B⊥k and θ=90°, and lines 508 and 518 with the configuration B⊥k using a circularly polarized beam. All the lines have been normalized to the total intensity of the beam $I_0$. The angle θ is the angle sketched in FIG. 2b which is defined as the angle between the laser beam polarization and the B field axis directions.

Although the spectra in the B∥k configuration 502, 512 just discussed have been collected using a linearly polarized laser, they do not depend on the particular polarization state of the beam (they are only due to the transversal nature of the electromagnetic waves) and one would expect to obtain the same results using for instance a completely depolarized source.

Figure 5C:
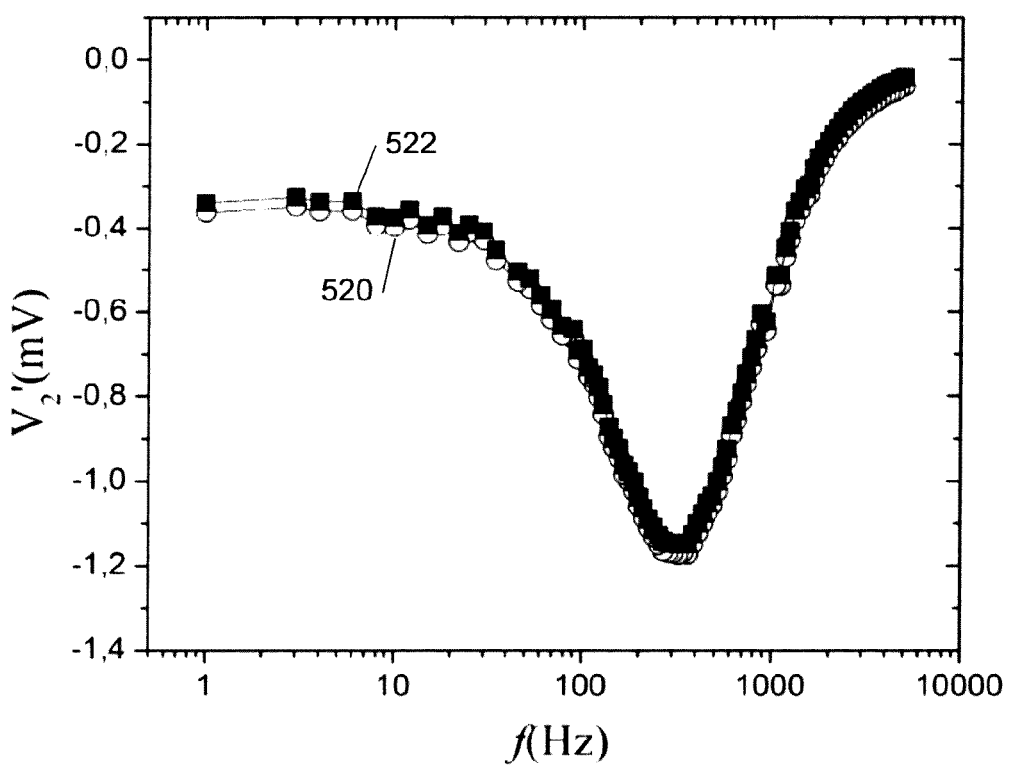

The hypothesis was checked using a circularly polarized beam, obtained through the insertion of a quarter ($\pi/4$) retarder in the optical path preceding the optical reservoir (principal axes of the retarder at 45° with respect to the polarization direction of the beam generated by the laser source). The results of these measurements are indeed identical to those in FIG. 5a as shown in FIG. 5c, where the in-phase $V_2'$ signal measured with a B∥k and θ=90° configuration is displayed as line 520 and in-phase $V_2'$ signal measured with a B∥k and circular polarization configuration is displayed as line 522.

For side-to-side comparison of the spectra, data are normalized to the average intensity $I_0$ of the transmitted beam. If the laser beam is linearly polarized perpendicular to the applied AC field direction, B⊥k and θ=90°, the signal shows the same features as for the configuration B∥k discussed above since more light is transmitted when the chains are aligned with the AC field that is perpendicular to the polarization direction. Conversely, using a light beam linearly polarized parallel to the applied field, namely B⊥k and θ=0°, the light scattering mechanism is maximized by aligning, at high field, the long axis of the MNBs formed chains parallel to the electric field of the laser beam and, thus, to achieve a better signal contrast. As a confirmation of the dichroic effect, meaning that different light polarization components are differently scattered, if a circularly polarized light beam is used, a lower signal, but having the same sign of the θ=0° can be recorded (B⊥k, unpolarized spectra in FIG. 5a).

Figure 6:
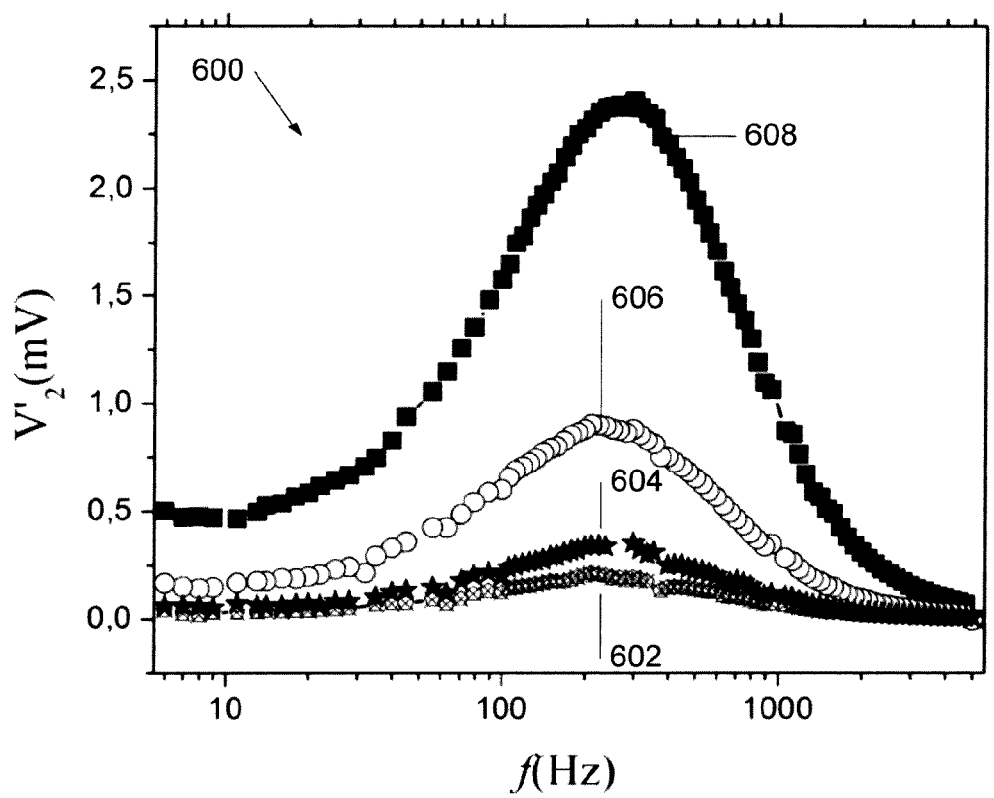
FIG. 6 shows the dependence on the particle concentration for the in-phase $2^{nd}$ harmonic signal.

FIG. 6 shows $V_2'$ signal 600 recorded for a suspension of 50 nm magnetic beads for different suspension concentration ranging from 1 μg/mL to 10 μg/mL measured in the configuration of B⊥k and θ=0° (thus a similar configuration as lines 502, 512 in FIGS. 6a-b) for an applied field of 2 mT. Line 602 represents a concentration of 1 μg/mL, line 604 a concentration of 2 μg/mL, line 606 a concentration of 5 μg/mL, and line 608 a concentration of 10 μg/mL. The magnetic nanoparticles may also be present in a concentration range of 0.1 μg/mL to 2000 μg/mL. Alternatively, the suspension concentration can be in the range of 0.1 μg/mL to 500 μg/mL, or in the range of 1 μg/mL to 50 μg/mL.

Figure 7:
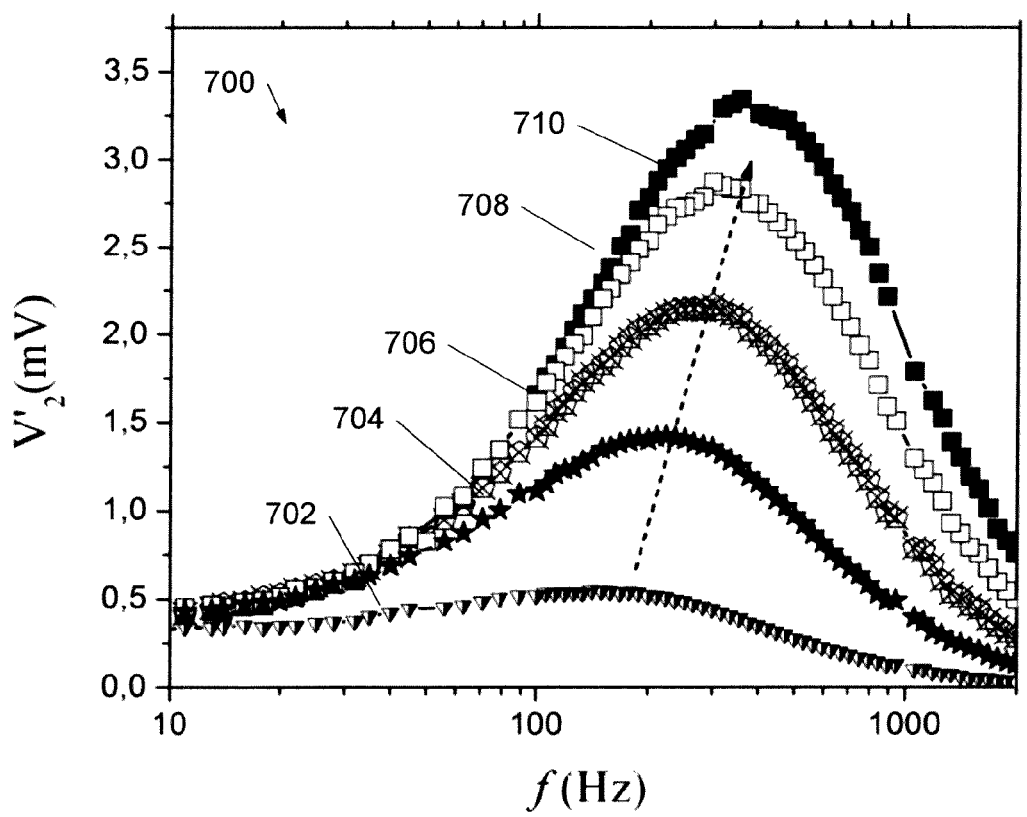
FIG. 7 shows the dependence of the magnetic field amplitude for the in-phase $2^{nd}$ harmonic signal.

FIG. 7 shows $V_2'$ signal 700 recorded for 50 nm magnetic beads in a concentration 10 μg/mL for different values of the applied field amplitude ranging from 1 mT to 3 mT with line 702 representing an applied field amplitude of 1 mT, line 704 representing an applied field amplitude of 1.5 mT, line 706 representing an applied field amplitude of 2 mT, line 708 representing an applied field amplitude of 2.5 mT, and line 710 representing an applied field amplitude of 3 mT.

The $V_2'$ spectra in FIG. 7 show that, for the same MNBs suspension, the peak frequency value and the signal intensity increase with the amplitude of the AC field.

Figure 8:
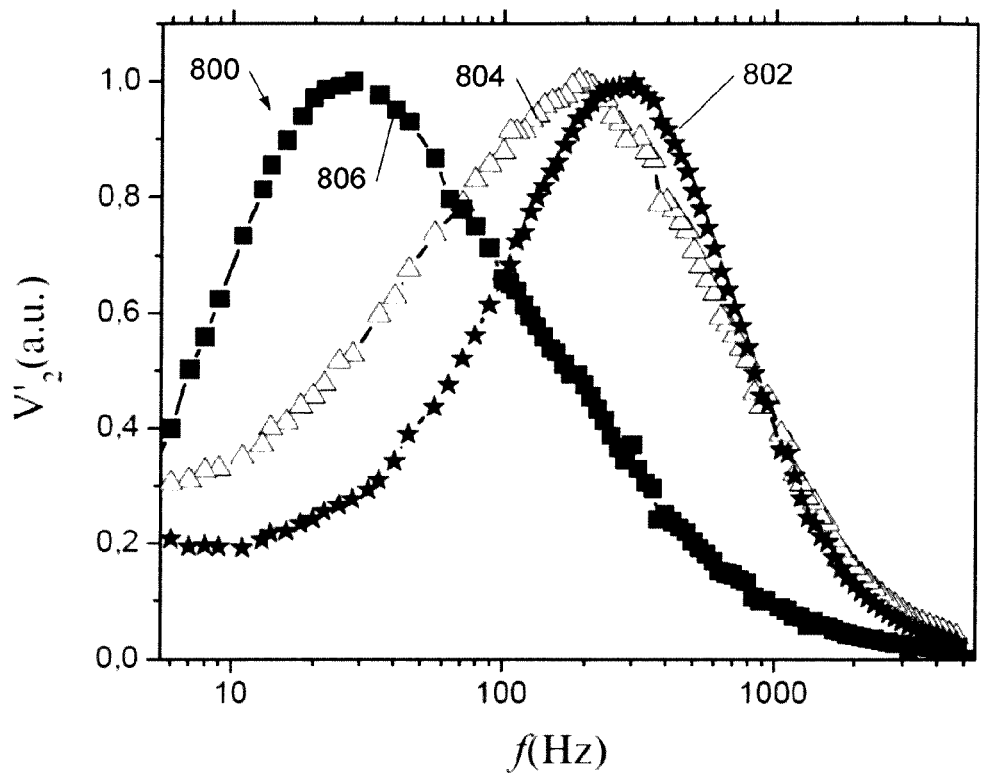
FIG. 8 shows the dependence of the particle size for the in-phase $2^{nd}$ harmonic signal.

FIG. 8 shows the comparison of the $V_2'$ spectra recorded in a measurement configuration B⊥k with θ=0° with varying size of the beads while keeping their concentration constant at 10 μg/mL as well as the amplitude of 2 mT of the AC field.

Line 802 is obtained with particles having a size of 50 nm, line 804 is obtained with particles having a size of 130 nm, and line 806 is obtained with particles having a size of 250 nm. For sake of clarity, the spectra have been normalized to their maximum value. The three MNB types show a similar behavior and three distinct value of $f_B$, being 21 Hz, 141 Hz and 233 Hz for particles having a size of 50 nm (line 802), 130 nm (line 804), and 250 nm (line 806), respectively.

In general the magnetic particles may have a diameter between 10 and 3000 nm, or between 20 and 1000 nm or between 50 and 250 nm.

A calculation of the average hydrodynamic diameter using Eq.(1) (for equivalent spheres at 300 K) gives hydrodynamic sizes of 122 nm (for the 50 nm MNBs), 144 nm (for the 130 nm MNBs) and 271 nm (250 nm MNBs). Dynamic light scattering measurements on the very same bead suspensions indicate a mean measured diameter for the beads of 114 nm, 126 nm and 250 nm (data not shown here).

Figure 9A:
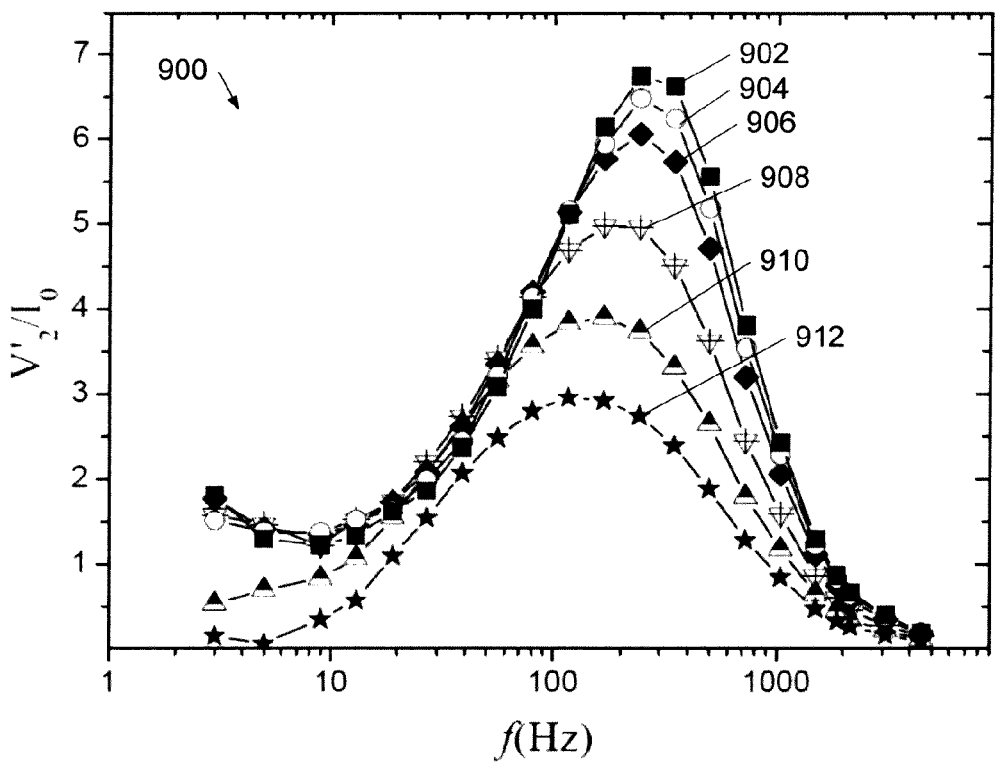
FIG. 9a shows in-phase $2^{nd}$ harmonic signals recorded for suspensions of streptavidin magnetic beads mixed with different concentrations of biotinylated BSA.

By monitoring $f_B$ it is possible to precisely characterize the mean hydrodynamic volume of the rotating MNB cluster suspension. In addition, by measuring the suspension under an applied field of 2 mT, the $V_2'$ component of the spectra peaks at a frequency value nearly corresponding to that expected from the $\chi'$ spectra from Eq. (1). This theoretical description is valid for MNBs having a remnant magnetic moment, while the behavior of completely superparamagnetic MNBs having similar sizes differs since the individual MNBs may not be subjected to Brownian relaxation To test the sensitivity of the setup in presence of a biological analyte, changes in the spectra were recorded when the formation of clusters was induced inside the MNBs suspension in presence of biotinylated bovine serum albumin. These results are shown for the in-phase $2^{nd}$ harmonic component in FIG. 9a. The data is obtained in a configuration where the magnetic field are propagating perpendicularly to the light, i.e. the detection configuration of FIG. 2b. A 20 μl suspension of 0.5 mg/ml Streptavidin coated Micromod Starch particles, having a nominal diameter of 80 nm, mixed with 20 μl sample containing different concentrations of biotinylated bovine serum albumin are shown in the figure. The samples have been left incubating for 10 minutes and then vials tubes have been inserted in a commercial magnetic separator until all particles were collected at the side of the tube. Particles were kept there in order to induce cluster formation. Finally, the suspension have been diluted to a total volume of 200 μl and measured. Suspensions of 80 nm (50 μg/mL) MNBS mixed with different concentrations of biotinylated BSA (bBSA) are obtained and the $V_2'$ signals 900 are measured after inducing MNB clustering with an external magnet. The signal is measured using blue light laser having a wavelength of 450 nm. The lines 902, 904, 906, 908, 910, and 912 represents a biotinylated BSA concentration of 0 pM, 100 pM, 250 pM, 500 pM, 1000 pM, and 2000 pM, respectively.

Figure 9B:
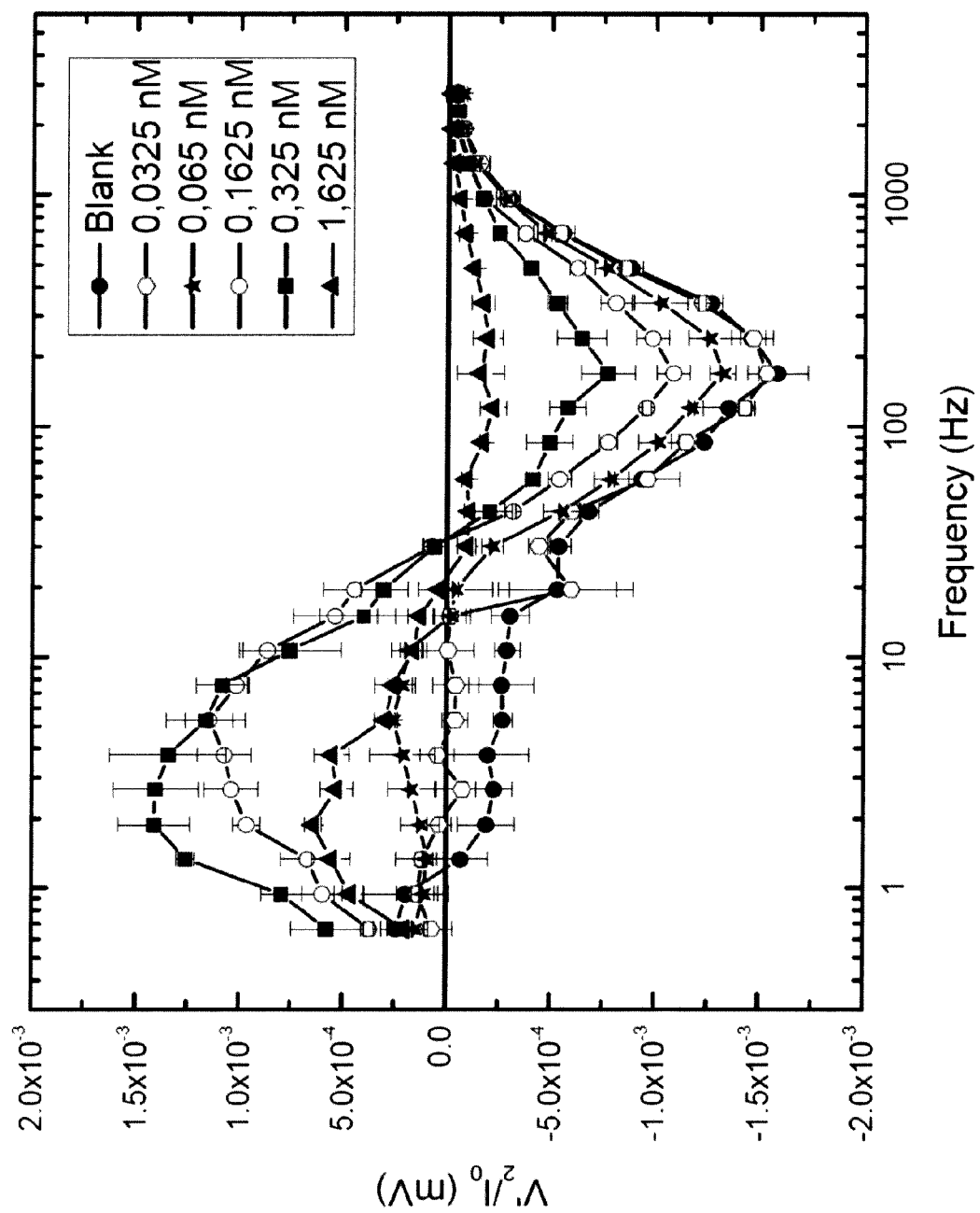
FIG. 9b shows in-phase $2^{nd}$ harmonic signals recorded for suspensions of magnetic beads mixed with different concentrations of biotinylated antibody.

FIG. 9b shows the in-phase component for biotinylated antibody detection using the configuration of FIG. 2a with a light beam propagating in parallel with the magnetic field. The blank signal shows a single peak, due to free magnetic beads rotating in suspension. When beads form clusters, an extra peak with opposite sign appears in the low frequency range of the spectra. This is due to clustered beads, which have opposite optical response to the external magnetic field excitation with respect to free beads. The light modulation created by the chain formation disruption dynamics of free beads have an opposite sign to the one of clustered beads, since they have different Mie scattering cross sections at 405 nm wavelength. As can be seen in FIG. 9b, the low-frequency peak having a positive sign increases in intensity as the concentration of the antibody increases until the concentration becomes quite large.

Thus, the data shown in FIG. 9b shows a strong increase in the sensitivity of the method as single and clustered beads can be easily distinguished and quantified.

For these measurements a blue light laser emitting at a wavelength of 450 nm is used in order to amplify the scattering effect and commercial cuvettes containing 200 μL of liquid, and having a total thickness crossed by the light of 5 mm were used. By adding a concentration of bBSA up to few nM shows that most of the beads form clusters in larger agglomerates, thus dramatically reducing the signal amplitude, and lowering the frequency peak at few Hz. Large agglomerates are able to follow the external field variation only at low frequencies and, when magnetically aligned they scatter less than single particles and this cause the strong reduction of the signal. At low concentration, only small agglomerates of particles are likely to be formed, and this is indicated by the lower frequency peak of the particle suspension. For this experiment, a consistent change in the signal can be observed down to bBSA concentration down to 100 pM.

Figure 10A:
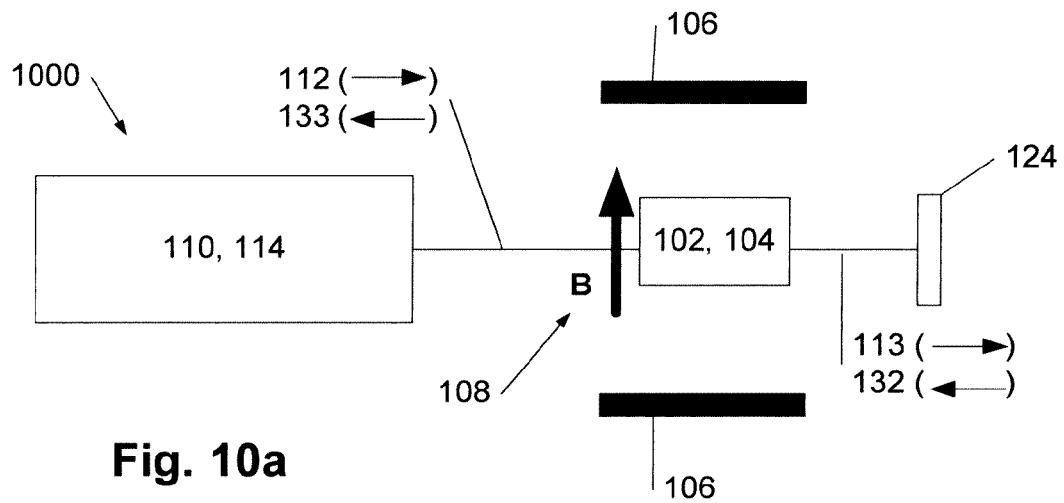
Figure 10B:
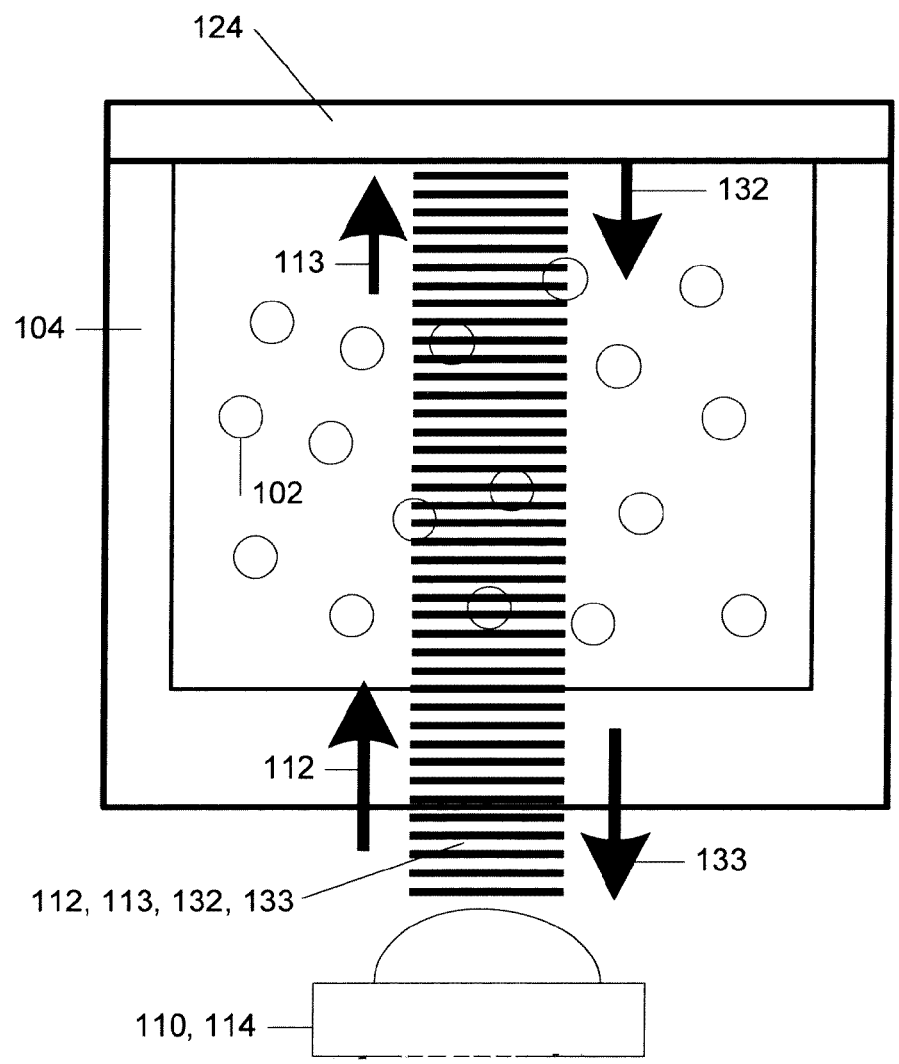

FIG. 10a illustrates a modified setup of a biosensor 1000 where FIG. 10b is a close-up view of the light-paths through the optical reservoir. In the modified setup 1000, a reflecting object 124, such as e.g. a mirror, is positioned such that the light transmitted through the solution of magnetic particles 102 in the optical reservoir 104 is reflected back (marked as item 132) through the optical reservoir 104 again by the reflecting object 124. The light 133 having passed the optical reservoir 104 at least twice is afterwards detected by the detection unit 114.

By having light, which passes the particles suspension 102 twice, the light scattered by the formation and disruption of magnetic particle chains driven by the external magnetic field is increased.

In FIGS. 10a-b, the detection unit 114 is shown as being integrated into the light source unit 110. This is however not a requirement and the two units could also be separated units. If the latter is the case, the transmitted light 133 having passed the optical reservoir 104 at least twice will have to be separated from the incoming light 112. This can be done in many different ways, by e.g. tilting the reflecting object 124 such that the light beams do not overlap spatially, or by inserting one or more objects, which direct the transmitted light 133 towards a separate detection unit 114.

In FIGS. 10a-b, the oscillating uniaxial magnetic field 108 is generated by a magnetic field generation unit 106 consisting of two electromagnets positioned in a B⊥k configuration compared to the light 112 from the light source 110. The parallel configuration could however equally well have been used.

Like in the setup shown and described in FIGS. 1-2, the magnetic particles suitable for use in the setup in FIGS. 10a-b can be functionalized with a bioactive ligand, such as e.g. antibodies, DNA, RNA, peptides, proteins, or protein complexes.

The magnetic particles will normally have a non-zero remnant magnetic moment and further be present in a suspension concentration in the range of 1 μg/mL to 50 μg/mL.

The magnetic particles can also be substantially spherical or have a more irregular shape. The substantially spherical magnetic particles may have a diameter between 10 and 3000 nm.

When using a biosensor as shown in FIG. 10a-b, the setup 1000 can be implemented in a DVD-type setup as shown and further explained in the following figures. The light source 110 in this kind of setup would then be a laser implemented in an optical pickup head, e.g. a CD, a DVD-ROM or a BLU-RAY optical pickup head. The laser light 112 would then be passed through a magnetic particle suspension inserted in between two electromagnets and then be reflected back to the pickup head photodetector by a mirror 124. In this way there is no need for any additional lens or photodetector to measure the transmitted light, since the optical drive can also be used as the detection unit.

When using the DVD-type setup, the light emitted by the pickup head is already polarized, thus simply enhancing the scattering effects from the magnetic fluid. Also, the pickup head already contains magnetic elements and coils and the photodetector is therefore already screened from the effects of magnetic fields.

Further, by removing the lenses already present in the DVD pickup head, a larger beam size (few mm in diameter) capable of interacting with a large quantity of particles is obtainable.

Figure 11:
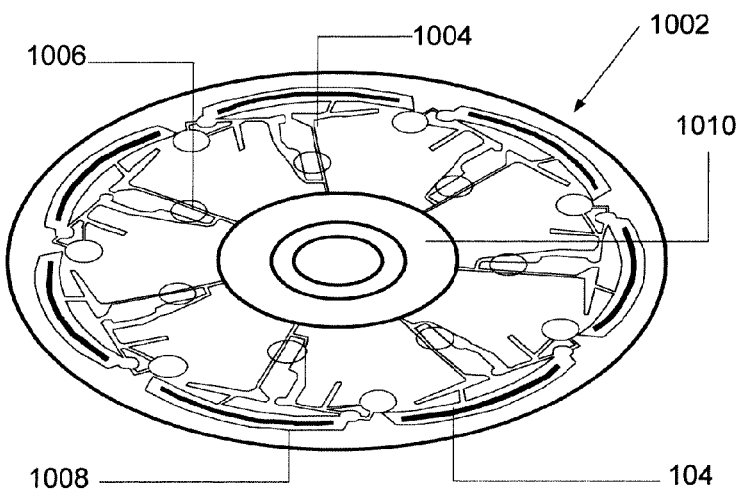
FIG. 11 shows a disc with embedded optical reservoirs.

In FIG. 11 is shown a disc 1002 with optical reservoirs implemented on it. The disc 1002 comprises at least one optical reservoir 1004, and at least one sample injection system for e.g. injection, dilution and mixing of the suspension of magnetic particles and the sample to be analyzed. The sample injection system may comprise at least one micro-needle 1006. The micro-needle 1006 is adapted for injection, dilution and mixing of the suspension of magnetic particles and the sample to be analyzed in at least one micro-channel 1004.

The biosensor described above can for all embodiments be used for diagnostic purposes. The biosensor could e.g. be used for analyzing blood, salvia, urine, water, plasma, or serum.

An injection point can be composed by at least one of the micro-needles 1006 which is used for collecting e.g. a blood sample from the user. The sample is centrifuged, diluted and mixed with a magnetic beads suspension through the dedicated centrifugal micro-channel system 1004.

The disc 1002 may comprise a plurality of microfluidic systems. The functionalized magnetic particles 102 in each of the plurality of optical reservoirs 104 can be different from the functionalized magnetic particles in the other optical reservoirs or be similar. This allows for simultaneous detection of multiple samples.

Figure 12A:
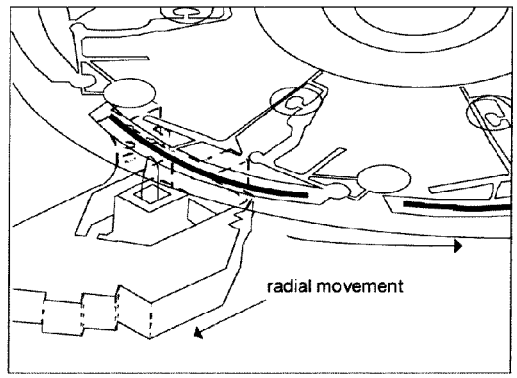
FIGS. 12a-b show close-up views of the disc for measurements in two positions on the disc.
Figure 12B:
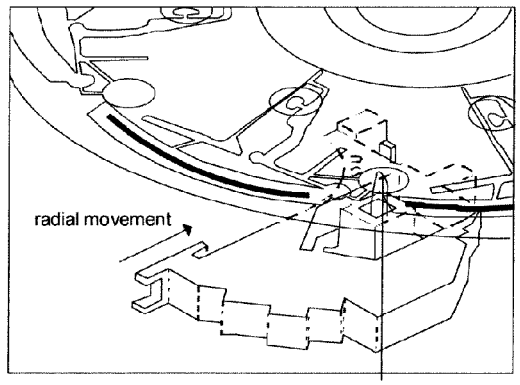

The disc may also comprise a corresponding reference optical reservoir 1014 for each optical reservoir 104, which is shown in FIGS. 12a-b. The reference optical reservoir 1014 contains the same amount and type of particles 102 as the corresponding optical reservoir 104, however, the reference optical reservoir 1014 is not mixed with the sample to be analysed, but is instead used for calculating the baseline and/or the background signal.

The biosensor may also comprise a motor adapted for rotating the disc and thereby the plurality of optical reservoirs 104 such that simultaneous or sequential analysis of the functionalized magnetic particles in each of the plurality of optical reservoirs 104 each positioned at different coordinates on the disc surface can be performed.

The disc 1002 further comprises one or more digital track area 1008 positioned on the surface of the disc 1002, where each of the digital track areas 1008 stores information about the position of each of the plurality of optical reservoirs 104 on the disc surface and/or the type of functionalized magnetic particles 102 contained in each of the optical reservoirs 104.

Multiple measurements can be performed simply by moving the optical pickup unit (which contains the light source 110 and the detection unit 114) along the radial direction. The embedded linear motor of commercial Blu-ray discs can e.g. be used for this operation. Several optical reservoirs 104 containing differently functionalized magnetic particles 102 can thus be measured simply using disc rotation and linear movement of the optical pickup unit. All the operations—including the mixing of the sample with the particles 102 can be performed simply using the rotational speed of the disc 1002.

In operation, the micro-fluidic system drives 20 μL of sample into each micro-channel 1004. The sample is driven by centrifugal force through the micro-channels 1004 into sensing reservoirs, which are separated by micro-capillary valves that can be opened when spinning the platform at certain angular frequencies. The sample, for example blood, can be separated into plasma and then mixed with magnetic particles in the micro-valves.

In each optical reservoir 104, around 10 μL of sample is mixed with a similar amount of magnetic particles 102, specifically functionalized to target specific biomolecules in each optical reservoir 104.

A combination of centrifugal forces and magnetic forces, provided by a permanent magnet or an electromagnet lying close to disk, are used to efficiently mix the particles 102 with the sample in order to achieve the highest efficiency in particle-target recognition.

The most external part of the disc 1002, where one or more optical reservoirs 104 are located, rotates in between two coils that are used for exciting the magnetic particles 102 for the final step of detection.

The magnetic coils will normally be integrated into the equipment containing the light source and the detection unit when using a disc. Another possibility is however to embed the magnet or electromagnet directly inside the disc 1002.

A typical measurement time for each optical reservoir is on the order of few minutes.

In addition, the presented invention can be integrated with other sensing elements embedded in the centrifugal disk platform that make use of the DVD pickup head as readout system.

By using the linear stage motor which is normally integrated in the optical drive unit, it is possible to scan multiple chambers at different radii each containing a predefined type of functionalized beads positioned at different coordinates on the disk surface.

Figure 13:
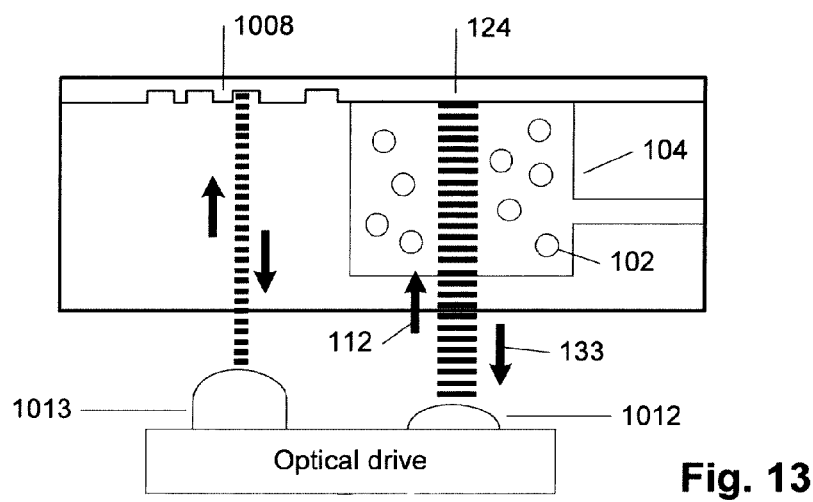
FIG. 13 shows a close-up of a two light source biosensor setup.

The biosensor may also comprise a double light source setup comprised in the disc reader device, where two light sources—a first light source e.g. emitting Blu-ray laser light 1012 and a second light source e.g. emitting DVD laser light 1013—are used for, respectively, analogically measure the magnetic beads and digitally track the position of the optical reservoirs 104 on the surface of the disc 1002. This is shown in FIG. 13. Thus, alternating the two light sources, thereby allows for simultaneous measurement of modulated transmitted light from the optical reservoirs 104 and tracking of the position of the optical reservoir 104 on the disc surface.

Further, using Blu-ray optical unit emitting blue light enhances the scattering by magnetic nanoparticles and the Blu-ray pickup therefore heads provides a better signal to noise ratio. The combination of Blu-ray and DVD laser also offers interesting opportunities for digital assisted positioning and tracking of the sensing chambers.

Figure 14A:
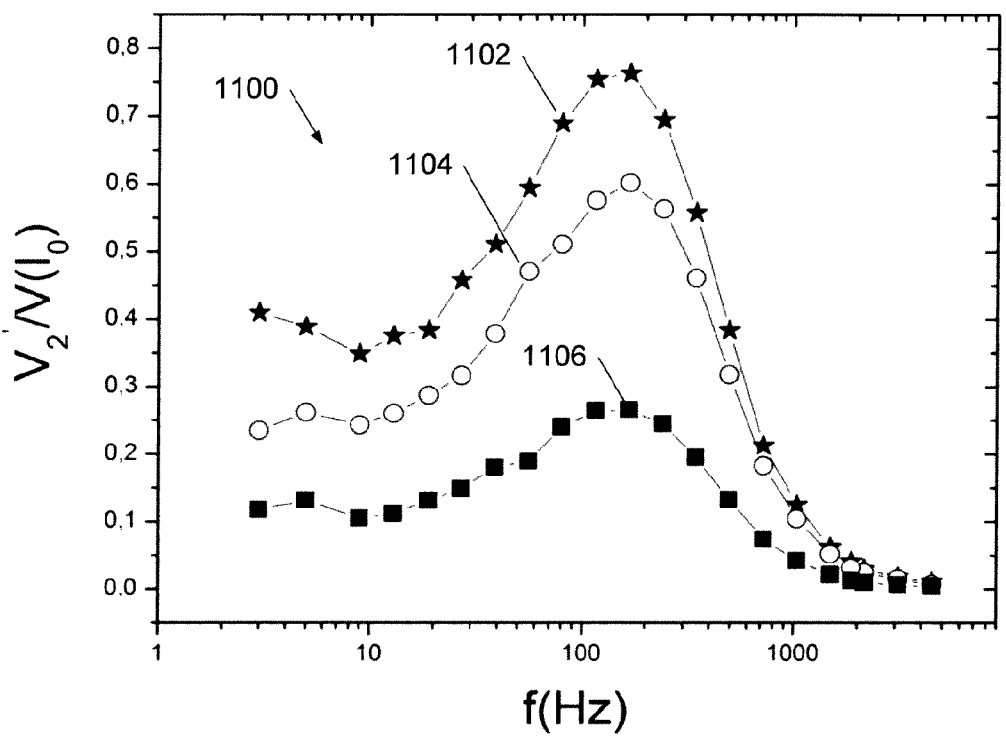
FIGS. 14a-b shows the in-phase $2^{nd}$ harmonic signals recorded for a suspension of magnetic beads mixed with different concentrations of biotinylated BSA, where the measurements are detected using a laser and a photodetector (FIG. 14a) and a DVD pickup head (FIG. 14b).
Figure 14B:
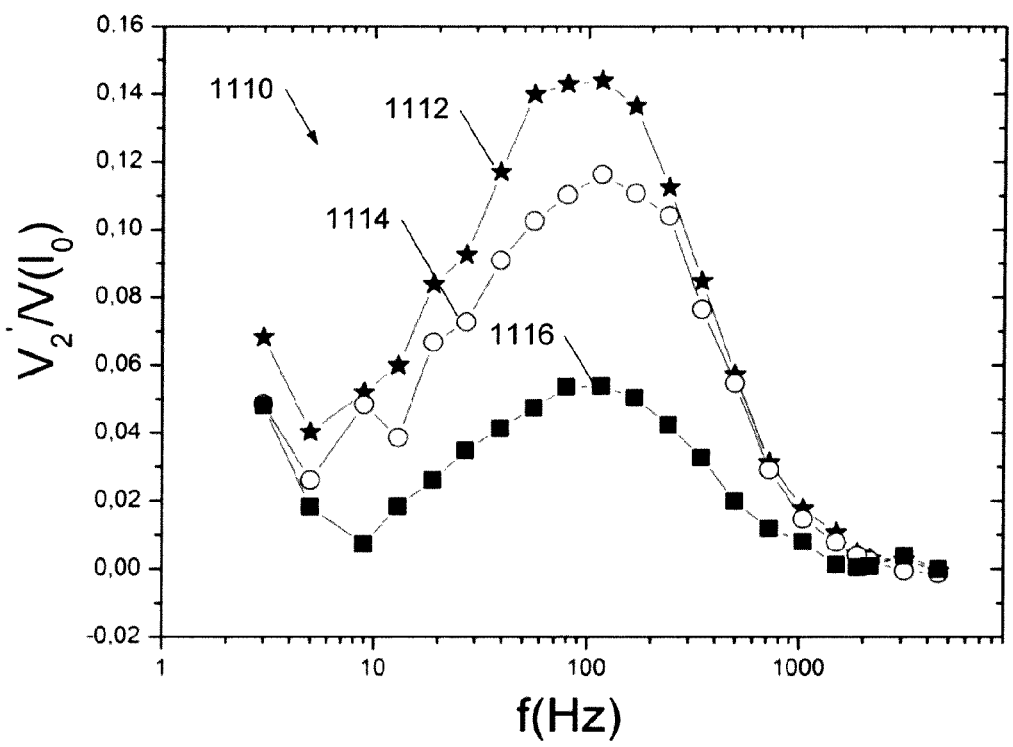

FIGS. 14*a-b* show the measurements on the same samples where a different concentration of bBSA protein is mixed together with magnetic nanobeads of a size of 100 nm. The in-phase components are recorded both using a laser and photodetector (1100 in FIG. 14*a*) and a DVD pickup head and a mirror as the reflecting object (1110 in FIG. 14*b*). Lines 1102/1112, 1104/1114, and 1106/1116 represents bBSA concentration of 0 pM, 80 pM and 160 pM, respectively. As seen by comparing the two graphs, a very similar result is observed, independently of which type of setup that is used.

Detection of biomarkers directly in plasma could also be imagined as well as measurements on magnetic beads directly in plasma, saliva, serum are also an option.

In the measurements, the setup of FIG. 1, FIG. 10*a* or FIG. 14*a* can be used.

The detection scheme used in the measurements may include a variation of the wavelength of the light from the light source and/or a switching on/off of the light and/or a modulation of the magnetic field at, where the signal, which is detected, is at an integer combination of the frequency of the modulation of the light from the light source and the frequency of the magnetic field.

The biosensor is primarily for measuring dynamic behaviours of magnetic particles driven by the oscillating uniaxial magnetic field. Alternatively, the biosensor can also be used for time-resolved measurements of the particles relaxation after the application of an external magnetic field.

Detection of the target molecule/cell/bacteria can be achieved by measuring the increase of the hydrodynamic diameter of the particles when the target molecules bind to the specifically functionalized particle surface.

Detection of the target molecule/cell/bacteria can also be achieved by target molecule induced aggregate formation of specifically functionalized magnetic particles of the same type (i.e. agglutination assay).

Further, detection of the target molecule/cell/bacteria may be achieved by target molecule induced aggregate formation of specifically functionalized particles of different types such as magnetic/nonmagnetic, particles of different sizes or by having fluorescent dyes on the surface. Microfluidic operations, as, for example centrifugation, size separation via electrical or magnetic field gradient, can be used to further separate different populations of particles or clustered particles from non-clustered ones, enabling the implementation of different types or readout schemes.

These are three of the most general way one can use this system as a biosensor.

REFERENCES

100 biosensor
102 solution of magnetic particles
104 optical reservoir
106 magnetic field generation unit
108 oscillating uniaxial magnetic field
110 light source
112 light from the light source
113 transmitted light
114 detection unit
116 photodiode
118 lock-in amplifier
120 gauss meter
122 polarizer
124 reflecting object, e.g. a mirror
132 reflected transmitted light
133 transmitted light having passed the optical reservoir at least twice
200 temporal variation of the transmitted light
202 oscillating external magnetic field waveform
204 measured AC component of the photodetector signal under the oscillating magnetic field
206 measured AC component of the photodetector signal in absence of the oscillating magnetic field
300 Fast Fourier Transform (FFT) signal
400 $2^{nd}$ harmonic signal
402 in-phase component of the $2^{nd}$ harmonic signal
404 out-of-phase component of the $2^{nd}$ harmonic signal
412 fit of curve 402
414 fit of curve 404
500 in-phase component of the $2^{nd}$ harmonic signal 502 B∥k
504 B⊥k and θ=0°
506 B⊥k and θ=90°
508 B⊥k and circular polarization
510 out-of-phase component of the $2^{nd}$ harmonic signal
512 B∥k
514 B⊥k and θ=0°
516 B⊥k and θ=90°
518 B⊥k and circular polarization
520 B∥k and θ=90°
522 B∥k and circular polarization
600 in-phase component of the $2^{nd}$ harmonic signal
602 concentration of 1 μg/mL
604 concentration of 2 μg/mL
606 concentration of 5 μg/mL
608 concentration of 10 μg/mL
700 in-phase component of the $2^{nd}$ harmonic signal
702 applied field amplitude of 1 mT
704 applied field amplitude of 1.5 mT
706 applied field amplitude of 2 mT
708 applied field amplitude of 2.5 mT
710 applied field amplitude of 3 mT
800 in-phase component of the $2^{nd}$ harmonic signal
802 particles having a size of 50 nm
804 particles having a size of 130 nm
806 particles having a size of 250 nm
900 in-phase component of the $2^{nd}$ harmonic signal
902 biotinylated BSA concentration of 0 pM
904 biotinylated BSA concentration of 100 pM
906 biotinylated BSA concentration of 250 pM
908 biotinylated BSA concentration of 500 pM
910 biotinylated BSA concentration of 900 pM
912 biotinylated BSA concentration of 2000 pM
1000 modified biosensor
1002 disc
1004 micro-channel
1006 micro-needle
1008 digital track area
1010 optical drive
1012 first light source, e.g. a Blu-ray light source
1013 first light source, e.g. a DVD light source
1014 reference optical reservoir
1100 in-phase components are recorded both using a laser and photodetector
1102 bBSA concentration of 0 pM
1104 bBSA concentration of 80 pM
1106 bBSA concentration of 160 pM
1110 in-phase components are recorded both using a DVD pickup head and a mirror as the reflecting object
1112 bBSA concentration of 0 pM
1114 bBSA concentration of 80 pM
1116 bBSA concentration of 160 pM

The invention claimed is:

1. A biosensor comprising:
at least one optical reservoir containing a suspension of magnetic particles;
a light source emitting light at a wavelength λ, with an intensity I, the light being directed at the optical reservoir and being adapted for interacting with the suspension of magnetic particles, wherein the light source is an optical pickup head and wherein the light entering the optical reservoir has an intensity $I_{in}$ and light transmitted through the optical reservoir has an intensity $I_{trans}$;
a magnetic field generation unit generating an oscillating uniaxial magnetic field, the oscillating uniaxial magnetic field oscillating at a frequency $f_x$ being variable between a start frequency $f_{x,\,start}$ and an end frequency, $f_{x,\,end}$, the oscillating uniaxial magnetic field being applied to the optical reservoir containing the suspension of magnetic particles whereby the suspension of magnetic particles is modulated such that the intensity $I_{trans}$ of light transmitted through the suspension of magnetic particles is modulated compared to the intensity $I_{in}$ of the light entering the optical reservoir, wherein light from the light source and the oscillating uniaxial magnetic field is propagating substantially parallel along an incoming direction;
a reflecting object positioned such that
the modulated light transmitted through the suspension of magnetic particles in the optical reservoir, and/or
light transmitted through the optical reservoir without being modulated by the suspension of magnetic particles
is reflected back through the optical reservoir by the reflecting object along a direction of propagation being substantially parallel with the incoming direction, and
a detection unit measuring the intensity $I_{trans}$ of the light transmitted through the suspension of magnetic particles in the optical reservoir after the light has passed through the optical reservoir at least two times,
wherein the intensity $I_{trans}$ of the transmitted light is detected at a frequency $f_y$ varying between a start frequency $f_{y,\,start}$ and an end frequency $f_{y,\,end}$ as the oscillating uniaxial magnetic field is swept from the start frequency $f_{x,\,start}$ to the end frequency $f_{x,\,end}$, wherein the detected frequency $f_y$ is the second harmonic ($f_y=2f_x$) or higher harmonic components of the intensity $I_{trans}$ of the transmitted light.

2. The biosensor according to claim 1, further comprising a microfluidic system comprising:
at least one optical reservoir, and
at least one sample injection system configured for injection, dilution and mixing of the suspension of magnetic particles and the sample to be analyzed.

3. The biosensor according to claim 1, comprising a plurality of optical reservoirs and/or microfluidic systems implemented on a disc.

4. The biosensor according to claim 3, wherein the plurality of optical reservoirs contains functionalized magnetic particles, wherein the functionalized magnetic particles in each of the plurality of optical reservoirs can be different from the functionalized magnetic particles in the other optical reservoirs or be identical to the functionalized magnetic particles in the other optical reservoirs.

5. The biosensor according to claim 3 further comprising:
a motor adapted for rotating the plurality of optical reservoirs such that simultaneous analysis of the functionalized magnetic particles in each of the plurality of optical reservoirs each positioned at different coordinates on the disc surface is possible, and
a digital track area positioned on the disc surface, each of the digital track area storing information about the position of each of the plurality of optical reservoirs on the disc surface and/or the type of functionalized magnetic particles contained in each of the optical reservoirs.

6. The biosensor according to claim 1, wherein the magnetic field generation unit is an electromagnet generating a time varying magnetic field between $f_{x,\,start}$=0.1 Hz and $f_{x,end}$=10 kHz, the magnetic field having a magnetic field intensity between 0.1 mT and 5 mT.

7. The biosensor according to claim 1, wherein the light source and the detection unit is integrated into the optical pickup head.

8. The biosensor according to claim 7, wherein the optical pickup head is from/in a compact disc reader device, a CD player/recorder, a DVD player/recorder or a Blu-ray player/recorder.

9. The biosensor according to claim 8, wherein DVD laser light and Blu-ray laser light from or in a compact disc reader device is alternated thereby allowing for simultaneous measurement of modulated transmitted light from the optical reservoirs and tracking of the position of the optical reservoir on the disc surface.

10. A method of analyzing blood, salvia, urine, water, plasma, or serum for a target molecule comprising:
   providing the biosensor of claim 1;
   contacting said biosensor with blood, salvia, urine, water, plasma, or serum containing said target molecule; and
   detecting target molecule induced aggregate formation thereby detecting the presence of said target molecule in said blood, salvia, urine, water, plasma, or serum.

\* \* \* \* \*